(12) United States Patent
Zhang

(10) Patent No.: US 10,018,098 B2
(45) Date of Patent: Jul. 10, 2018

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 118 days.

(21) Appl. No.: 15/098,751

(22) Filed: Apr. 14, 2016

(65) Prior Publication Data

US 2017/0298801 A1 Oct. 19, 2017

(51) Int. Cl.
*F01N 3/00* (2006.01)
*F01N 11/00* (2006.01)
*F01N 3/033* (2006.01)

(52) U.S. Cl.
CPC .............. *F01N 11/00* (2013.01); *F01N 3/033* (2013.01)

(58) Field of Classification Search
CPC ........................... F01N 2560/05; F22B 37/008
See application file for complete search history.

(56) References Cited

U.S. PATENT DOCUMENTS

| 5,451,769 A | 9/1995 | McAdoo et al. |
| 7,520,173 B2 | 4/2009 | Lee et al. |
| 8,310,249 B2 | 11/2012 | Paterson |
| 8,823,401 B2 | 9/2014 | Roth et al. |
| 9,778,160 B2 * | 10/2017 | Zhang ................ G01N 15/0656 |
| 2009/0188300 A1 | 7/2009 | Gualtieri et al. |
| 2012/0085146 A1 | 4/2012 | Maeda et al. |
| 2015/0355066 A1 | 12/2015 | Zhang |

FOREIGN PATENT DOCUMENTS

| DE | 4001048 A1 * | 7/1991 | ............. G01N 27/16 |
| DE | 102008041038 A1 | 2/2010 | |

OTHER PUBLICATIONS

Machine English translation of DE4001048A1.*
Zhang, Xiaogang, "Method and System for Exhaust Particulate Matter Sensing," U.S. Appl. No. 14/835,270, filed Aug. 25, 2015, 50 pages.

* cited by examiner

*Primary Examiner* — Mark Laurenzi
*Assistant Examiner* — Jason Sheppard
(74) *Attorney, Agent, or Firm* — Julia Voutyras; McCoy Russell LLP

(57) ABSTRACT

Methods and systems are provided for a particulate matter sensor positioned downstream of a diesel particulate filter in an exhaust system. In one example, a particulate matter sensor may include a spherical assembly including a hollow rod and a plurality of flow tubes connected to diametrically opposite ends of the assembly, and a sensor element positioned within the assembly, distal to the plurality of flow tubes, thus protecting the sensor element from contaminants and water droplets condensing at or near the plurality of flow tubes. In addition, the support rod may further include a drainage hole to flow larger particulates out the spherical assembly and out into the exhaust passage.

16 Claims, 11 Drawing Sheets

METHOD AND SYSTEM FOR EXHAUST PARTICULATE MATTER SENSING

FIELD

The present application relates to sensing particulate matter in an exhaust system.

BACKGROUND/SUMMARY

Engine emission control systems may utilize various exhaust sensors. One example sensor may be a particulate matter sensor, which indicates particulate matter mass and/or concentration in the exhaust gas. In one example, the particulate matter sensor may operate by accumulating particulate matter over time and providing an indication of the degree of accumulation as a measure of exhaust particulate matter levels. The particulate matter sensor may be located upstream and/or downstream of a diesel particulate filler, and may be used to sense particulate matter loading on the particulate filter and diagnose operation of the particulate filter.

One example of a PM sensor is shown by Maeda et. al. in US 20120085146 A1. Therein, the particulate matter sensor is attached to the top of an exhaust pipe and housed within a cylindrical protection tube. The PM sensor additionally includes a sensor element that is positioned closer to a center of the exhaust pipe so that the sensor output more reasonably represents an average soot concentration in the exhaust pipe. In addition, the PM sensor includes inlet apertures configured to direct the exhaust into the sensor and towards the sensor element. Herein, the sensor element is positioned closer to the inlet holes to allow the sensor element to capture more of the incoming particulates.

However, the inventors have recognized potential issues with such sensor configurations. As one example, such an arrangement may make the sensor element more vulnerable to being contaminated by water droplets in the exhaust condensing at or near the inlet apertures. In such sensor configurations, additional protective coating may be required to protect the soot sensor element from direct impingement of larger particulates and water droplets. Adding additional protective layer may reduce the electrostatic attraction between the charged soot particles and the electrodes of the sensor element and may lead to reduced soot sensor sensitivity. With reduced sensitivity, the soot sensor may not be able to determine the leakage of the particulate filter in a reliable way. Thus, errors in the sensor may lead to a false indication of DPF degradation and unwarranted replacement of functioning filters.

On the other hand, if the sensor is mounted at the bottom of the exhaust pipe, as shown by Paterson in U.S. Pat. No. 8,310,249 B2, water condensing at the bottom of the exhaust pipe may overflow into the sensor element thereby contaminating the sensor element. Such contamination of the sensor element may lead to fluctuations in the output of the sensor, thereby decreasing the accuracy of estimating particulate loading on the particulate filter.

The inventors herein have recognized the above issues and identified an approach to at least partly address the issues. In one example approach, a particulate matter sensor for sensing particulate matter in an exhaust passage of an engine is provided. The particulate matter sensor comprises a spherical assembly, a support rod coupled to a bottom end of the spherical assembly, a plurality of flow tubes coupled to a top end of the spherical assembly, and a sensor element positioned within the spherical assembly, distal to the plurality of flow tubes. In this way, by separating the plurality of flow tubes from the sensor element, issues related to water droplets and larger contaminants impinging on the sensor element and causing fluctuations in the sensor output may be reduced.

As one example, an exhaust particulate matter sensor assembly may be positioned downstream of an exhaust particulate filter in an exhaust pipe. The particulate matter sensor may include a spherical assembly including a plurality of flow tubes attached to a top end of the assembly, and a sensor element positioned closer to a bottom end of the assembly. Specifically, the spherical assembly may include hollow spherical concentric outer and inner devices separated by a gap. A hollow support rod may be installed at the bottom end of the assembly coupling the assembly to a bottom of the exhaust pipe. By mounting the assembly on the support rod, the sensor element may be positioned closer to a center of the exhaust pipe.

The plurality of flow tubes coupled to the top of the assembly may include hollow cylindrical inner and outer tubes. As such, the outer tube may be an inlet tube mounted on top of the outer device and the inner tube may be an exit tube mounted on top of the inner device and positioned within the outer tube. In addition, the outer tube may include a plurality of perforations along the curved surface configured to direct the exhaust into the gap between the outer and the inner devices. Subsequently, the exhaust may be split into two portions; a larger portion of the exhaust inside the gap may be directed towards the sensor element positioned within the inner device via a hole located at the bottom of the inner device, and a smaller portion may be gravitated towards the bottom of the outer device. Herein, the smaller portion may include particulates having a larger than threshold size and hence may gravitate towards the bottom of the outer device. However, hollow rod is fluidically coupled to the outer device. Hence, the heavier particulates in the smaller portion of the exhaust may flow into the hollow rod, and further be drained out of the assembly. However, lighter soot particles in the larger portion of the exhaust may enter the inner device and may accumulate at the sensor element. As such, the sensor element may in turn be used to diagnose the functioning of the particulate filter. Herein, the sensor element is positioned away from the inlet tube and thus, by distancing the sensor element from the inlet tube, and further providing an alternative path for the heavier particulates, the sensor element may be protected and the sensor reliability may be increased.

In this way, the functioning of the sensor element may be improved and the sensor may be rendered more reliable. In addition, by enabling a more accurate diagnosis of the exhaust particulate filter, exhaust emissions compliance may be improved. This reduces the high warranty costs of replacing functional particulate filters. The exhaust may exit the sensor via the outlet tubes positioned on top of the assembly. The symmetrical design of the inlet and the outlet tube eliminate manufacture process for specific sensor orientation at the installation and enhance the sensor repeatability.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
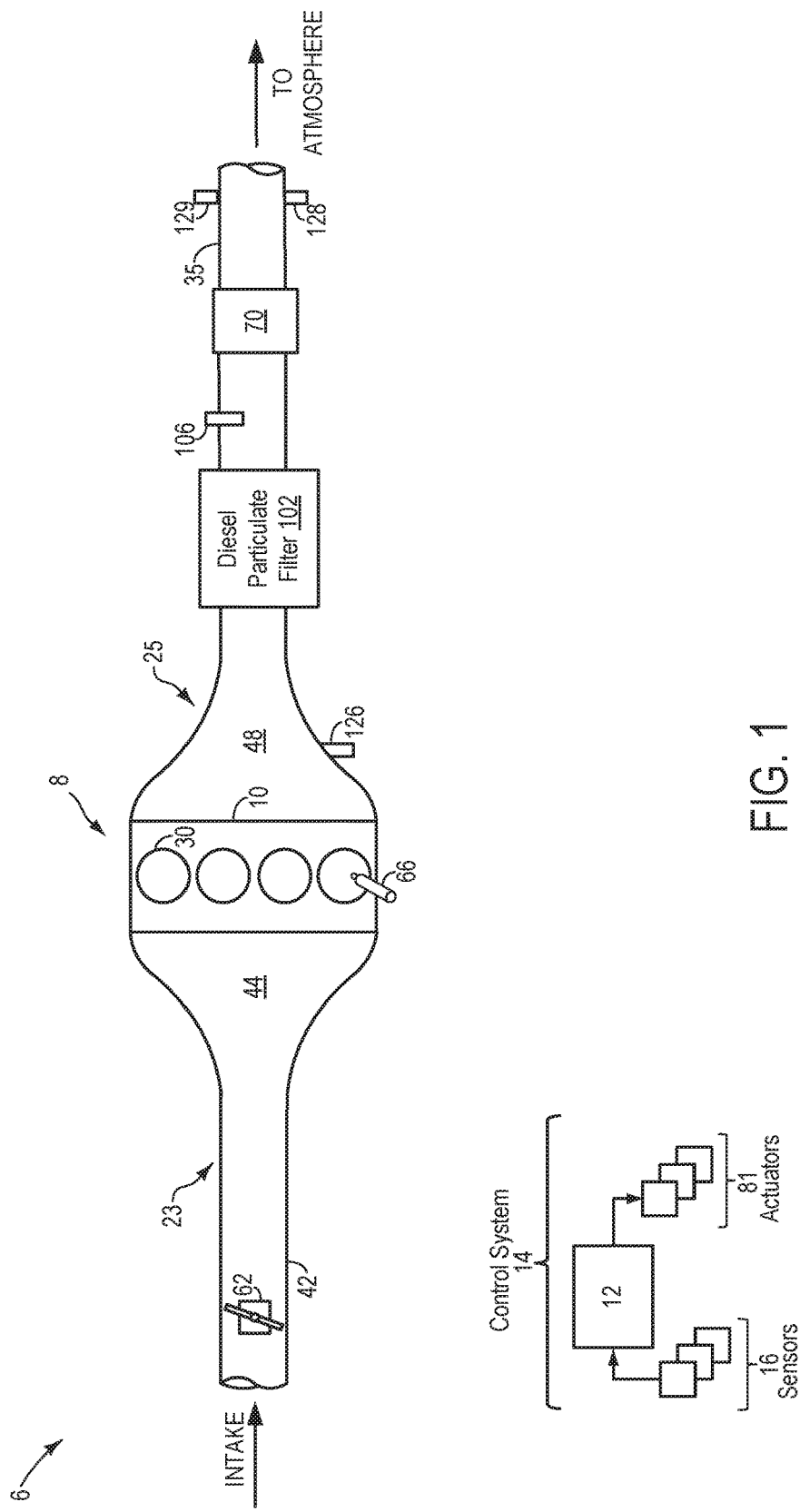
FIG. 1 shows a schematic diagram of an engine and an associated particulate matter (PM) sensor positioned in an exhaust flow.
Figure 2A:
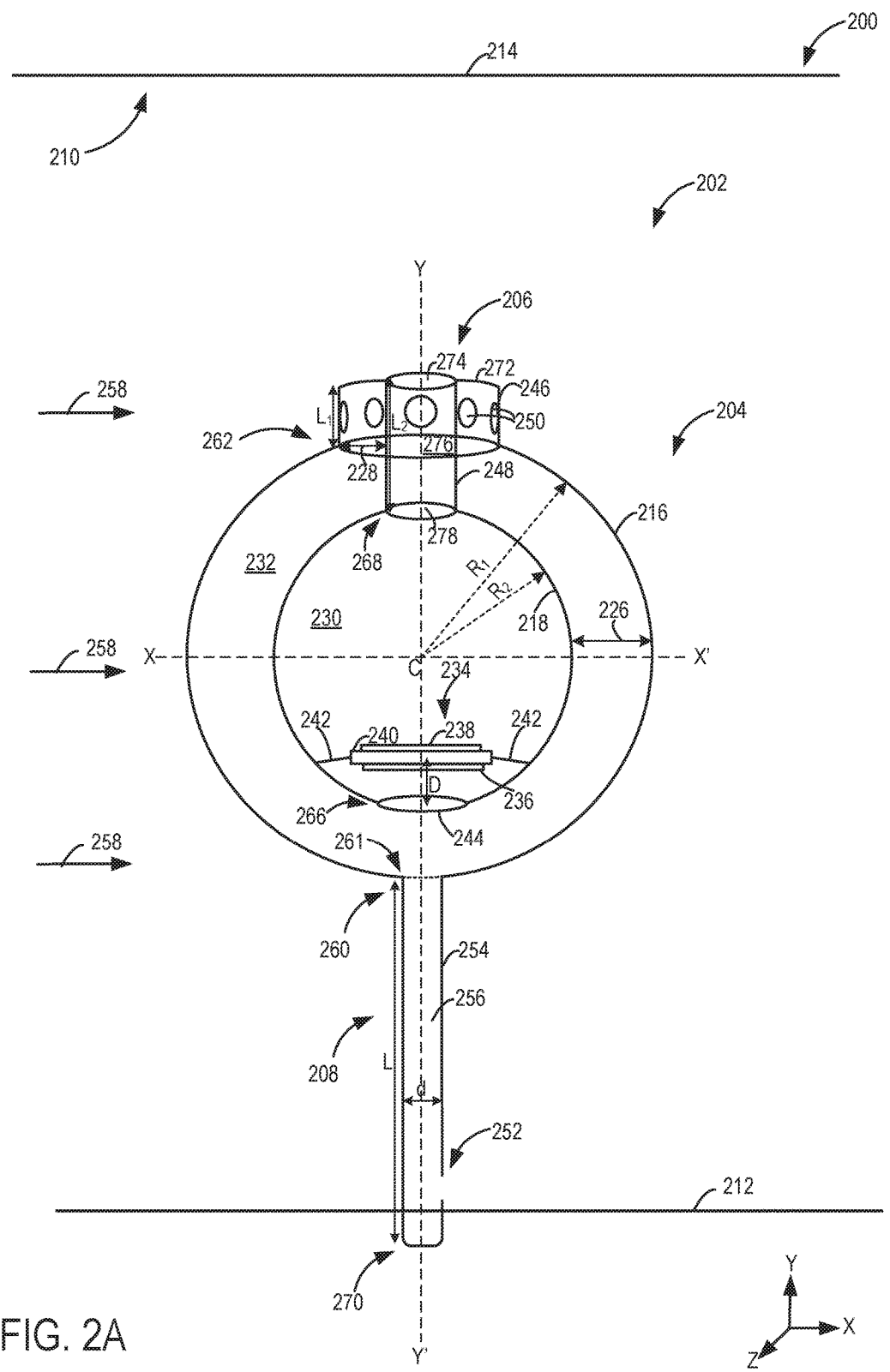
FIG. 2A shows a schematic diagram of the PM sensor including a spherical assembly having a plurality of flow tubes and a sensor element mounted inside an exhaust pipe via a hollow support rod.
Figure 2B:
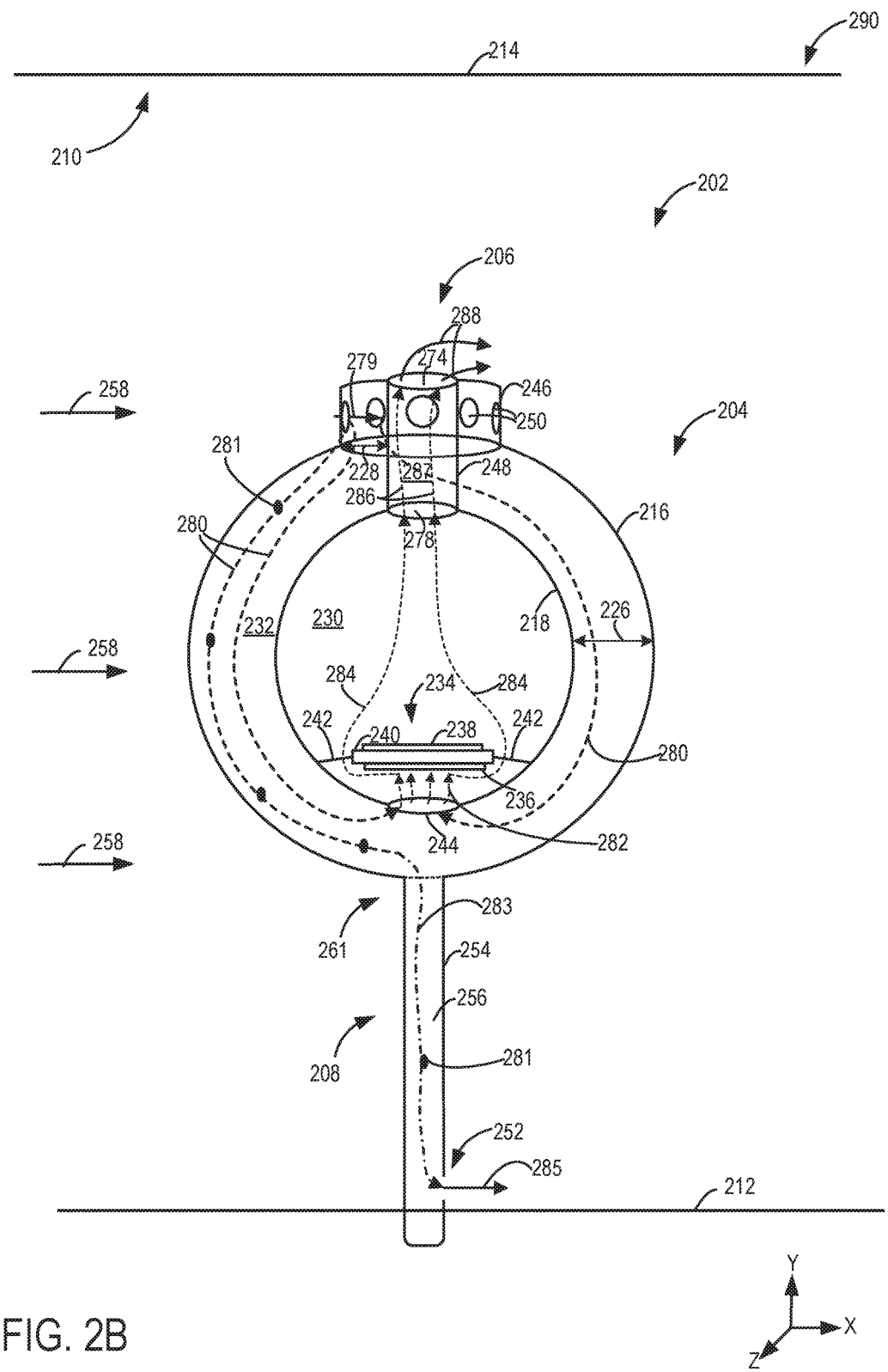
FIG. 2B shows a schematic diagram of the PM sensor showing exhaust flowing into the PM sensor via flow tubes attached to a top of the spherical assembly.
Figure 3A:
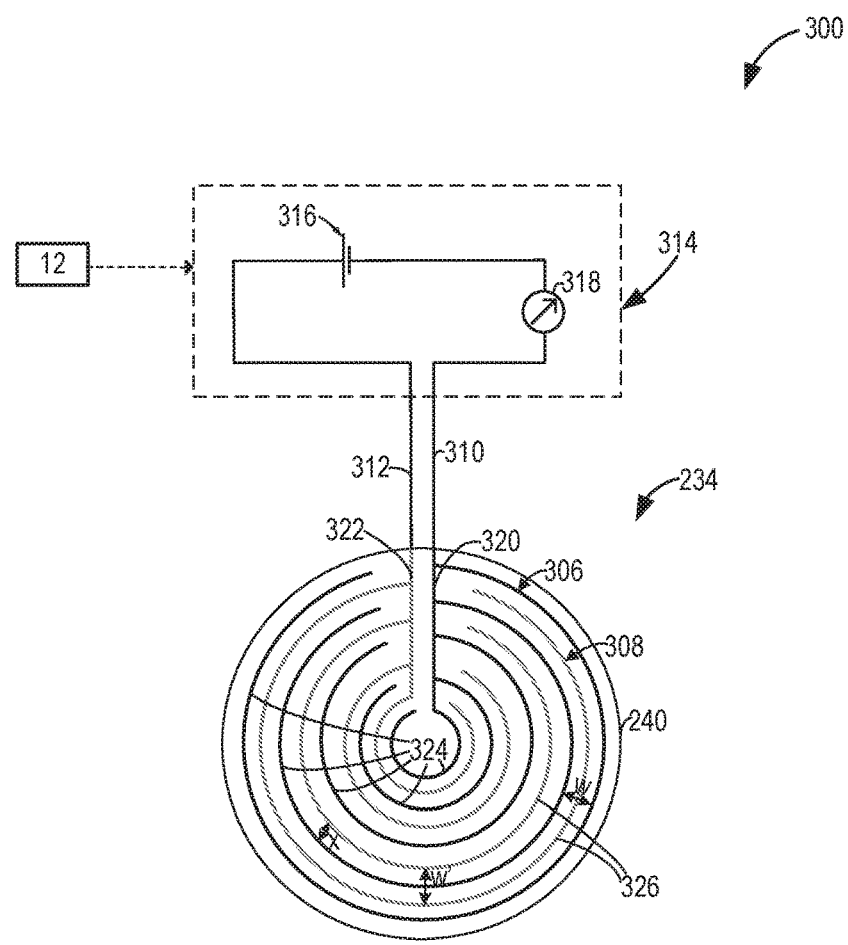
FIGS. 3A-3C show example layouts of circular interdigitated electrodes formed on a first surface of the sensor element.
Figure 3B:
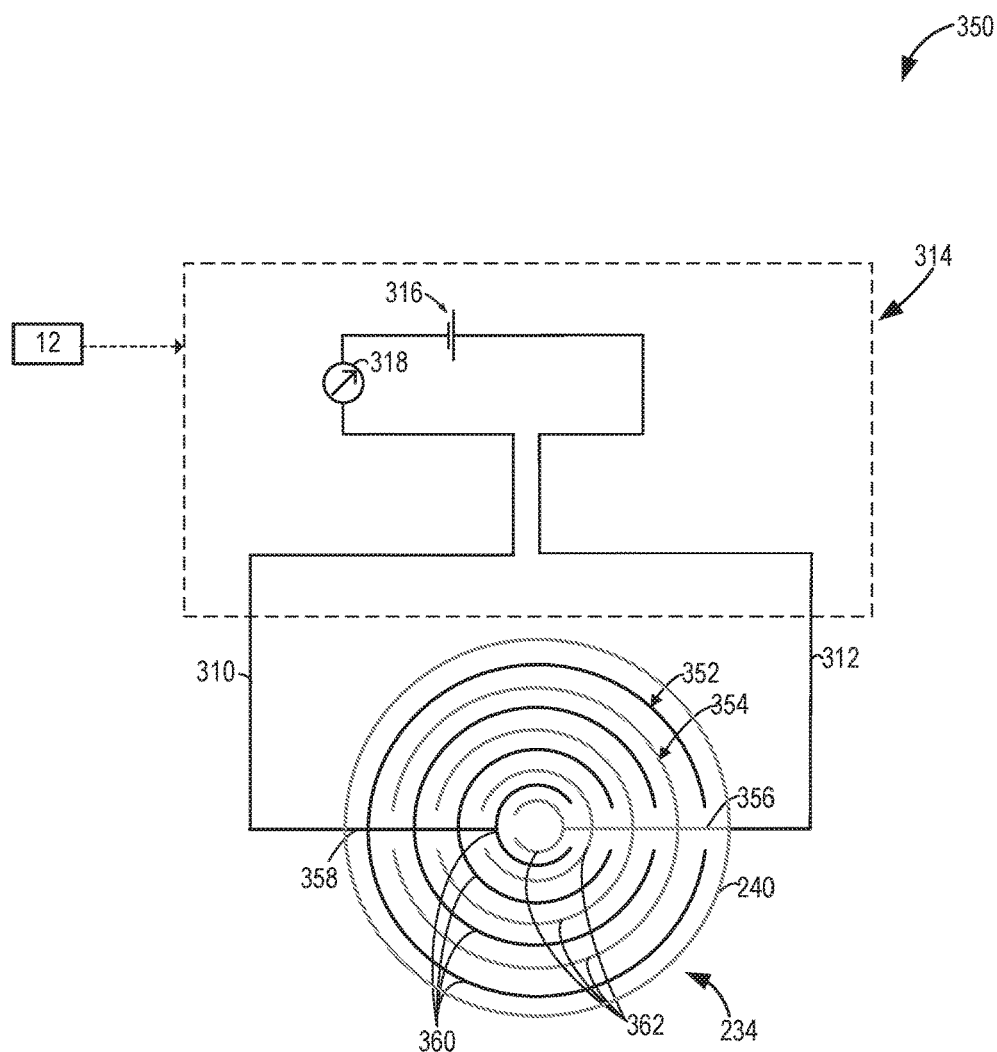
Figure 3C:
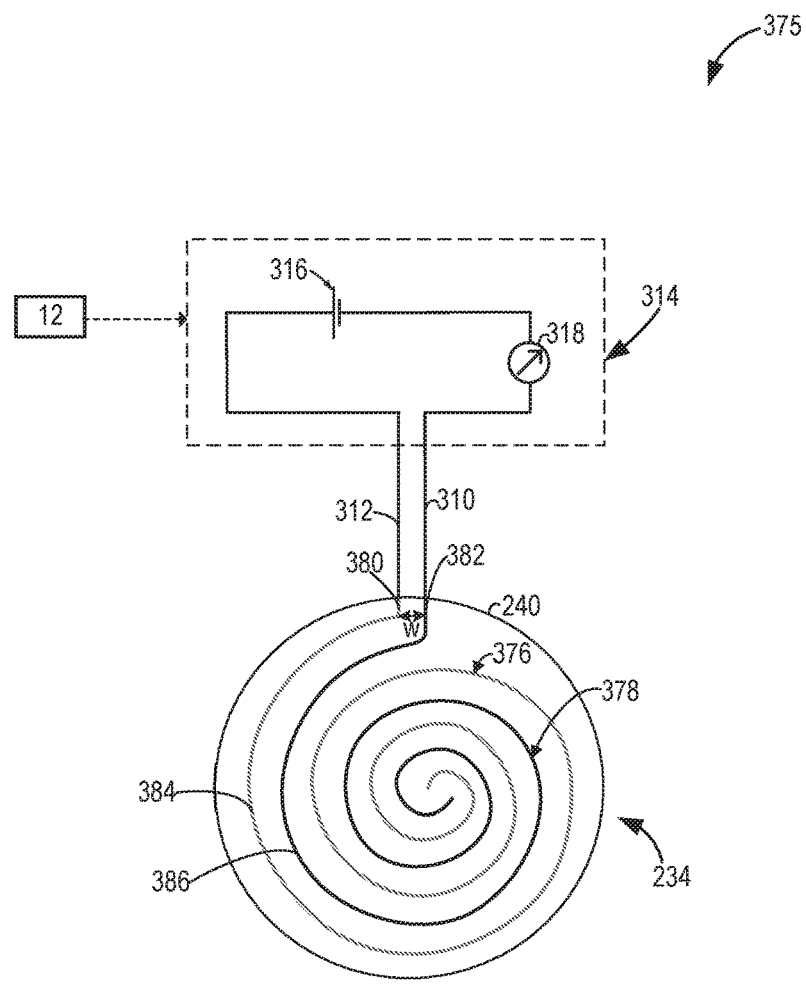
Figure 4:
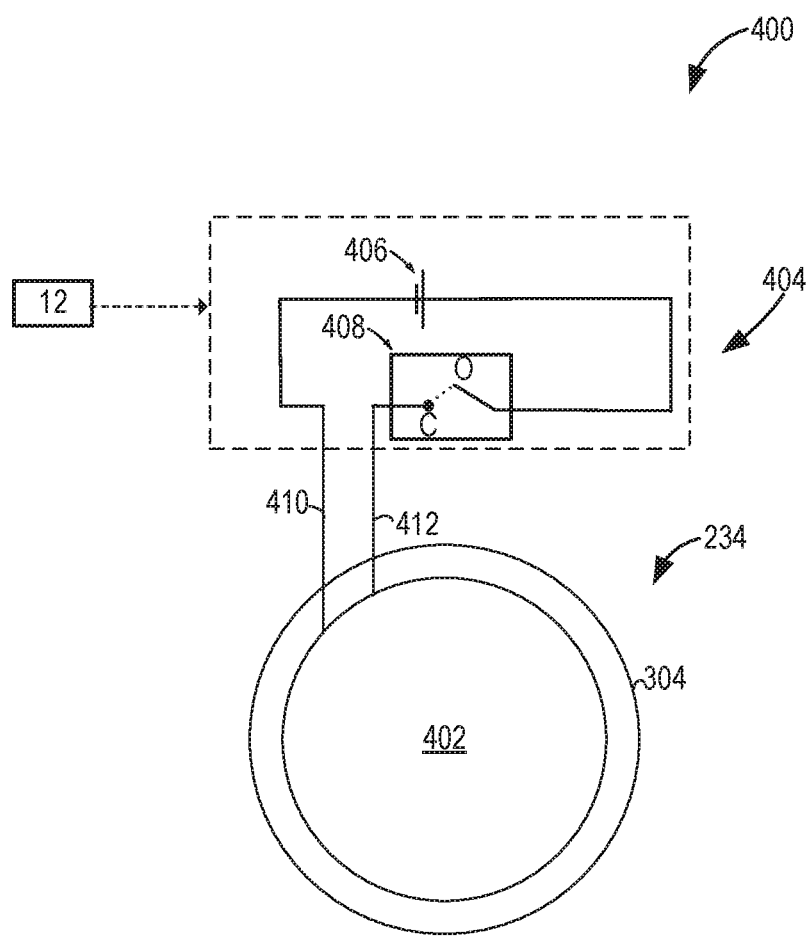
FIG. 4 shows a heating element formed on a second, opposite surface of the sensor element.

The following description relates to systems and methods for sensing particulate matter (PM) in an exhaust flow of an engine system, such as the engine system shown in FIG. 1. A PM sensor may be placed in an exhaust passage of the engine system. The PM sensor may include a spherical assembly including a plurality of flow tubes attached and a support rod attached to diametrically opposite ends of the spherical assembly. The spherical assembly may be mounted to a bottom of the exhaust passage with the help of the support rod. Specifically, the spherical assembly includes an inner spherical device positioned within an outer spherical device and separated by a gap and the plurality of flow tubes includes an inner tube positioned within an outer tube and separated by a space, as shown in FIG. 2A. Further, a circular spherical element may be positioned inside the inner device, and exhaust may be directed towards the sensor element with the aid of perforations and holes formed on the outer tube and the inner device as shown in FIG. 2B. The sensor element may include concentric interdigitated electrodes formed on a first surface of the sensor element as shown in FIGS. 3A-3C. Additionally, the sensor element may include heating elements formed on a second, opposite surface as shown in FIG. 4. A controller may be configured to perform a control routine, such as an example routine of FIG. 5 to accumulate particulates in the exhaust across the electrodes of the sensor element.

Further, the controller may intermittently clean the PM sensor (FIG. 6) to enable continued PM monitoring. Furthermore, the controller may be configured to perform a routine, such as an example routine of FIG. 7 to regenerate the exhaust particulate filter based on a time between PM sensor regenerations. An example of filter diagnostics is shown in FIG. 8. In this way, the functioning of the PM sensor to estimate the filtering capabilities of the DPF (and thereby to detect DPF leaks) may be increased.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. As an example, while operating the PM sensor to accumulate soot particulates, the controller may send a control signal to an electric circuit to apply a voltage to the sensor electrodes of the PM sensor to trap the charged particulates onto the surface of the sensor electrodes. As another example, during PM sensor regeneration, the controller may send a control signal to a regeneration circuit to close a switch in the regeneration circuit for a threshold time to apply a voltage to heating elements coupled to the sensor electrodes to heat the sensor electrodes. In this way, the sensor electrodes are heated to burn off soot particles deposited on the surface of the sensor electrodes. Example routines are described herein with reference to FIGS. 5-7.

Turning now to FIG. 2A, a schematic view 200 of an example embodiment of a particulate matter (PM) sensor assembly 202 (such as PM sensor 106 of FIG. 1) is shown. The PM sensor assembly 202 may be configured to measure PM mass and/or concentration in the exhaust gas, and as such, may be coupled to an exhaust passage 210 (e.g., such as the exhaust passage 35 shown in FIG. 1), upstream or downstream of a diesel particulate filter (such as DPF 102 shown in FIG. 1).

In the schematic view 200, the PM sensor assembly 202 is disposed inside the exhaust passage 210 with exhaust gases flowing (along X-axis) from downstream of the diesel particulate filter towards an exhaust tailpipe, as indicated by arrows 258. The PM sensor assembly 202 includes a spherical assembly 204 (hereafter interchangeably referred to as assembly 204) mounted inside the exhaust passage 210 via a hollow support rod 208 (hereafter the hollow support rod may be interchangeably referred to as a support rod, a mounting rod, or a hollow rod). In addition, the spherical assembly 204 is coupled to a plurality of flow tubes 206 via a top portion 262 of the assembly 204, and includes a sensor element 234 positioned within the assembly 204. Herein, the assembly 204 is spherical in shape. As another example, the assembly may be a hollow elliptical structure positioned within the exhaust passage.

The hollow support rod 208 may extend along the Y-axis in a direction orthogonal to a long axis of the exhaust passage 210. A length L of the support rod 208 may be much larger than a diameter d of the support rod 208. Further, the support rod 208 may include a top end 260 and a bottom end 270, and as such, the length L may include the distance between the top end 260 and the bottom end 270 of the support rod 208. A portion of the bottom end 270 may be coupled to a bottom 212 (and not coupled to a top 214 of the exhaust passage 210, for example) of the exhaust passage 210. As an example, the portion of the bottom end 270 of the support rod 208 extending into the bottom 212 of the exhaust passage 210 may be much smaller than the portion 254 of the support rod 208 remaining inside the exhaust passage 210. The bottom end 270 of the support rod 208 may be installed in the bottom 212 of the exhaust passage 210 in a number of ways. For example, the bottom end 270 of the support rod 208 may be inserted, screwed, or held to the bottom 212 via additional screws (not shown). The support rod 208 may include a drainage hole 252 located closer to the bottom end 270 of the support rod than the top end 260. Though depicted as a single hole 252, the drainage hole may include a plurality of holes in some example embodiments. The purpose of the drainage hole 252 is to drain out particulates having a larger than threshold size from the PM sensor assembly 202, which will be described in detail later.

During cold start of the vehicle, the exhaust may not be warm enough to convert water inside the exhaust pipe into steam (gaseous state), and thus water may continue to remain in the liquid state and collect at the bottom 212 of the exhaust passage 210. By mounting the assembly on the support rod 208 as described below, the PM sensor assembly 202 may be positioned closer to the center of the exhaust passage and the sensor may be protected from water condensing and collecting at the bottom of the exhaust passage.

The top end 260 of the support rod 208 may be coupled to a bottom portion of the spherical assembly 204. As such, the top end 260 of the support rod 208 may be open (indicated by dashed line in FIG. 2A) in order to allow for fluidic coupling between the support rod 208 and the spherical assembly 204. Specifically, the spherical assembly 204 includes a hollow outer spherical device 216 (henceforth referred to as outer device 216) and a hollow inner spherical device 218 (henceforth referred to as inner device 218) positioned concentrically within the outer device 216. The top end 260 of the support rod 208 may be coupled to a bottom portion or end 261 of the outer device 216. As a result, the support rod 208 is fluidically coupled to the outer device 216 specifically at the opening formed in the bottom portion 261 of the outer device 216 and the top end 260 of the support rod 208. It may be appreciated that the support rod 208 is not coupled to the inner device 218 but coupled only to the outer device 216.

The outer device 216 is a spherical protection device of radius $R_1$. Likewise, the inner device 218 is a spherical protection device of radius $R_2$. The inner device 218 is positioned concentrically within the outer device 216 such that there is a gap 226 between the inner and the outer device. Herein, the inner device 218 is smaller than the outer device 216 (e.g., $R_2 < R_1$), and the gap 226 between the outer device 216 and the inner device 218 is equal to a difference in the radii of the two spherical devices (e.g., $R_1 - R_2$). As such, the inner device 218 may be held to the outer device 216 by screws (not shown) located along the circumference of the outer device 216, for example. The outer device 216 and the inner device 218 may share a common center C, and include a common central axis Y-Y' that is perpendicular to the direction of exhaust flow (arrow 258) inside the exhaust passage 210. The inner device 218 and the outer device 216 may be symmetrically positioned with respect to each other. Together the inner device 218 and the outer device 216 form the spherical assembly 204 of the PM sensor assembly 202.

As an example, the length L of the support rod 208 and the radii $R_1$ and $R_2$ of the outer and inner devices of the spherical assembly 204 may be selected such that the spherical assembly 204 may be positioned closer to a center of the exhaust passage 210. In this way, by positioning the sensor assembly close to the center of the exhaust passage 210, the average soot particulate concentration in the exhaust passage 210 may be reasonably represented in the sensor assembly. Thus, the sensitivity of the PM sensor assembly 202 may be increased and the sensor may be rendered more reliable. In addition, by enabling a more accurate diagnosis of the exhaust particulate filter, exhaust emissions compliance may be improved. As such, this reduces the high warranty costs of replacing functional particulate filters, exhaust emissions are improved, and exhaust component life is extended.

As mentioned previously, the spherical assembly 204 includes a plurality of flow tubes 206 attached to the top portion 262 of the assembly. Specifically, the flow tubes 206 include an outer tube 246 and an inner tube 248. The outer tube 246 is an inlet tube configured to receive exhaust from the exhaust passage 210, and the inner tube 246 is an outlet or exit tube configured to release the exhaust from the PM sensor assembly 202 back into the exhaust passage 210. Herein, the outer tube 246 is a hollow cylinder of length $L_1$ and radius $R_3$. Likewise, the inner outlet or exit tube 248 is a hollow cylinder of a length $L_2$ and radius $R_4$ placed coaxially within the outer tube 246, and separated from the outer tube 246 by a space 228. Herein, the inner tube 248 is smaller than the outer tube 246 (e.g., $R_4 < R_3$), and the space 228 between the inner tube 248 and the outer tube 246 is equal to a difference in the radii of the two tubes (e.g., $R_3 - R_4$). As such, the inner tube 248 may be held to the outer tube 246 by screws (not shown) located along side surfaces of the outer tube 246, for example. The outer tube 246 and the inner tube 248 may share a common central axis Y-Y' that is common to the central axis of the spherical assembly 204. The central axis Y-Y' is perpendicular to the direction of exhaust flow (arrow 258) inside the exhaust passage 210 as described earlier.

The length $L_2$ of the inner tube 248 may be longer than the length $L_1$ of the outer tube 248 (e.g., $L_2 > L_1$). Thus, the inner tube 248 traverses the gap 226 formed between the inner device 218 and the outer device 216. The outer tube 246 includes a top surface 272 and a bottom surface 276, and the distance from the top surface 272 to the bottom surface 276 corresponds to the length $L_1$ of the outer tube 246. Likewise, the inner tube 248 includes a top surface 274 and a bottom surface 278, and the distance from the top surface 274 to the bottom surface 278 corresponds to the length $L_2$ of the inner tube 248. Herein, the bottom surface 276 of the outer tube 246 is coupled to the top portion or end 262 of the spherical assembly 204. Specifically, the coupling between the bottom surface 276 of the outer tube 246 and the top portion 262 of the outer device 216 allows for fluidic communication between space 228 and the gap 226. It may be appreciated that the top portion 262 of the spherical assembly 204 corresponds to the top portion of the outer device 216. Thus, the outer tube 246 is coupled to the outer device 216 but not to the inner device 218 of the spherical assembly 204. Said another way, the outer device 216 includes the outer tube 246 and the support rod 208 coupled to a diametrically opposite ends or portions of the outer device 216.

Further, the top surface 272 of the outer tube 246 is coplanar with the top surface 274 of the inner tube 248. However, the bottom surface 276 of the outer tube 246 is not coplanar with the bottom surface 278 of the inner tube 248. As such, the bottom surface 278 of the inner tube 248 is at a distance (equal to the gap 226, for example) below the bottom surface 276 of the outer tube 246 and is further coupled to a top portion 268 of the inner device 218. To summarize, the top surfaces of the outer tube and the inner tube are coplanar but not coupled to either the outer or the inner devices of the spherical assembly and lie outside the spherical assembly. However, the bottom surface 276 of the outer tube 246 is coupled to the top portion of the outer device 216, while the bottom surface 278 of the inner tube 248 is coupled to the top portion of inner device 218. The top portion 268 of the inner device 218 is closer to the top portion 262 of the outer device 216 and further away from the bottom portion 261 of the outer device 216. The top portion 268 of the inner device 218 may be separated from the top portion 262 of the outer device 216 by a distance that is equal to the gap 226 between the outer and the inner devices, for example. Herein, the gap 226 may be equal to the difference in lengths between the outer and the inner tubes (e.g., $L_2 - L_1$).

The top surface 272 of the outer tube 246 may be sealed while the bottom surface 276 of the outer tube 246 may be open (or not sealed) thus fluidically coupling the outer tube 246 with the outer device 216. Herein, the space 228 formed between the outer tube 246 and the inner tube 248 is fluidically coupled to the gap 226 formed between the outer device 216 and the inner device 218. However, both the top surface 274 and the bottom surface 278 of the inner tube 248 may be open. Thus, the inner device 218 is fluidically coupled to the inner tube 248 via the bottom surface 278, and to the exhaust passage 210 via the top surface 274, for example.

The inner device 218 is coupled to the bottom surface 278 of the inner tube 248 at the top portion 268 as explained previously. In addition, a bottom portion 266 of the inner device 218 includes a hole (or aperture or orifice) 244. Herein, the hole 244 is formed on the inner device 218 is diametrically opposite to the top portion 268 of the inner device 218 that is coupled to the inner tube 248. Thus, the hole 244 is closer to the bottom portion 261 of the outer device 216 and further away from each of the top portion 262 of the outer device 216 and the top portion 268 of the inner device 218.

As such, the plurality of flow tubes 206 is configured to direct exhaust into and out of the spherical assembly 204. Specifically, the outer tube 246 includes a plurality of perforations or holes 250 formed along a curved surface of the outer tube 246 though which exhaust enter the assembly 204. Exhaust inside the spherical assembly exits the assembly via the inner tube 248 as explained in detail with reference to FIG. 2B.

As such, the outer device 216 may be manufactured as a hollow spherical device with cutouts formed on two diametrically opposite ends (along central Y-Y' axis). In one example, the cutouts may be circular in shape. On a top end, the radius of the cutout may be substantially equal to the radius $R_3$ of the outer tube 246. At a bottom end, the cutout may be smaller and substantially equal to the diameter d of the hollow support rod 208. The outer inlet tube may be manufactured as a hollow cylinder with radius $R_3$ and length $L_1$ and may be inserted into the top end of the outer device 216 at the cutout on the top end of the outer device, for example. Likewise, the support rod 208 may be manufactured as a hollow cylindrical rod of diameter d and length L and may be inserted into the bottom end of the outer device 216 at the bottom cutout. The opposite end of the hollow support rod may be mounted on the bottom 212 of the exhaust passage 212 as described previously.

Similar to the outer device, the inner device 218 may be manufactured as a hollow spherical device with cutouts formed on two diametrically opposite ends (along the central Y-Y' axis). On a top end, the radius of the cutout may be substantially equal to the radius $R_4$ of the inner tube 248. At a bottom end, the cutout may result in the hole 244. The inner outlet tube may be manufactured as a hollow cylinder with radius $R_4$ and length $L_2$ and may be inserted first into the outer tube 246 and then into the top end of the inner device 218 via the top cutout formed on the inner device 218. In addition, the inner device 218 may include a sensor element 234 suspendably coupled within the inner device 218 as explained below.

The sensor element 234 may be suspended closer to the hole 244 with the help of support legs 242. As an example, three supporting legs 242 (two of the three legs shown in the view 200) may be evenly distributed and coupled along the circumference of the inner device 218 (along an inner surface, for example). As such, one end of each of the supporting leg 242 may be coupled to the inner surface of the inner device 218 and opposite end of each of the supporting leg 242 may be coupled to the sensor element 234. Herein, a length and a spring constant of the supporting legs 242 may be adjusted so as to suspend the sensor element 234 at a distance D from the hole 244 formed on the inner device 218.

The sensor element 234 includes a substrate 240 having interdigitated electrodes 236 formed on a first surface, and a heating element 238 formed on a second, opposite surface. Said another way, the interdigitated electrodes 236 and the heating element 238 are formed on two opposite sides of the substrate, thus separated by a thickness of the substrate 240. As such, the sensor element 234 may be a circular element to take advantage of the spherical design of the assembly 204. However, the sensor element may be rectangular, square, triangular or the like without deviating from the scope of the invention. For a circular shaped element 234, the interdigitates electrodes 236 may additionally be circular so that there is increased surface area coverage of the electrodes formed on the circular sensor element 234. Various other geometries may alternatively be possible without deviating from the scope of the disclosure. An example geometry includes interdigitated "comb" electrode structure. The soot particulates in the exhaust may be deposited between the interdigitated electrodes as explained with reference to FIGS. 3A-3C. The sensor element 234 may be positioned within the inner device 218 such that the interdigitated electrodes 236 are facing the hole 244 while the heating element 238 that is formed on the opposite surface is further away from the hole 244. The sensor element 234 is positioned away from the flow tubes 206 of the spherical assembly 204. Thus, by separating the plurality of flow tubes from the sensor element, issues of water droplets and larger contaminants impinging on the sensor element and causing fluctuations in the sensor output may be reduced. Three example patterns of the circular interdigitated electrodes are shown in FIGS. 3A-3C. As such, the description of the electric circuit and the composition of the sensor element and the substrate are common to FIGS. 3A-3C.

Turning now to FIG. 3A, a schematic view 300 of a bottom of the sensor element 234 of FIG. 2A and an accompanying electric circuit 314 is shown. Specifically, circular interdigitated electrodes formed on a circular substrate 240 are shown. Since the protection assembly is spherical in shape, it may be advantageous to include a circular substrate for the sensor element to increase the surface area available for soot particulate adsorption. However, various other geometries of the substrate and the electrode layout may be possible without deviating from the scope of the invention. Some example layouts include rectangular or square substrate with interdigitated comb electrodes.

In view 300, the substrate 240 of the sensor element 234 is circular with radius R. The substrate 240 of the sensor element 234 may be manufactured from electrically insulating materials. Some examples of possible electrically insulating materials may include oxides such as alumina, zirconia, yttria, lanthanum oxide, silica, and combinations comprising at least one of the foregoing, or any like material capable of inhibiting electrical communication and providing physical protection for the electrodes 306 and 308. In some examples, the substrate 240 may be composed of a porous ceramic material (e.g., porosity of about 60%). The radius R of the circular substrate 240 may be determined based on the radius $R_2$ of the inner device 218 and further adjusted based the distance D at which the sensor element 234 is suspended above the hole 244 as shown in FIG. 2A.

The sensor electrode 236 includes a pair of circular interdigitated electrodes 306 and 308 formed on one surface of the sensor element 234. Herein, the pair of planar interdigitated electrodes 306 and 308 may form circular interdigitated tines indicated by black and grey lines in view 300. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. Each electrode of the interdigitated pair may be composed of the same or different material as the other electrode of the pair. For example, the electrode 306 may be composed of the same material as the electrode 308. In another example, electrode 306 and electrode 308 may be composed of different materials. The spacing between the circular "tines" of the two electrodes may typically be in the range from 30 micrometers to 50 micrometers with the linewidth of each individual "tine" being about the same value, although the latter is not necessary.

The electrodes 306 and 308 may be connected via electrical connections to an electric circuit 314. The electrode 308 of the sensor element 234 is connected with connecting wire 312 to a positive terminal of a voltage source 316 of the electric circuit 314. Thus, the electrode 308 may be referred to as a positive electrode. Similarly, the electrode 306 of the sensor element 234 is connected to a measurement device 318 via a connecting wire 310, and further connected to a negative terminal of the voltage source 316 of the electric circuit 314. Thus, the electrode 306 may be referred to as a negative electrode. The interconnecting wires 310 and 312, the voltage source 316 and the measurement device 318 are part of the electric circuit 314 and are housed outside the exhaust passage 210 (as one example, <1 meter away). Further, the voltage source 316 and the measurement device 318 of the electric circuit 314 may be controlled by a controller, such as controller 12 of FIG. 1, so that particulate matter collected at the PM sensor assembly 202 may be used for diagnosing leaks in the DPF, for example. As such, the measurement device 318 may be any device capable of reading a resistance (or current) change across the electrodes, such as a voltmeter (or an ammeter). As PM or soot particles get deposited between the electrodes 306 and 308, the current measured between the electrodes 306 and 308 may start to increase, which is measured by the measurement device 318. The controller 12 may be able to determine the current and infer a corresponding PM or soot load on the electrodes 306 and 308 of the sensor element 234 of the PM sensor assembly 202. By monitoring the load on the sensor element 234, the exhaust soot load downstream of the DPF may be determined, and thereby used to diagnose and monitor the health and functioning of the DPF.

In FIG. 3A, electrode 306 includes a plurality of circular tines of increasing diameter from a center of the substrate 240. The electrode 306 (interchangeably referred to as the negative electrode) includes a substantially straight portion 320 connecting the electrode 306 to the interconnecting wire 310. Herein, the straight portion 320 may extend from the edge (located on the circumference, for example) of the substrate 240 inward towards the center of the substrate 240. As an example, a length of the straight portion 320 may be equal to the radius R of the substrate 240. The electrode 306 may additionally include a plurality of discrete curved portions 324 starting at certain locations along the straight portion 320 running clockwise along the surface of the substrate 240 and ending at a distance from the straight portion 320. Herein, each curved portion 324 corresponds to a major arc of a circle of certain radius with center coinciding with the center of the substrate 240, for example. As an example, an innermost curved portion of the negative electrode 306 may be formed at the center of the substrate 240. The innermost curved portion of the negative electrode 306 may include a major arc of radius r1. A second curved portion may be formed at a spacing w1 from the innermost curved portion and may include a major arc of radius r2 where r2=r1+w. Likewise, a third curved portion may be formed at a spacing w from the second curved portion, and may further include a major arc of radius r3, wherein r3=r2+w=r1+2w. In a similar way, successive curved portions may be formed at the spacing w, and with increasing radii. Mathematically, the radius of the nth curved portion 324 of the negative electrode 306 may be given by equation (1):

$$r_n = r1 + (n-1)*w \qquad (1)$$

The number, n of the curved portions 324 of the negative electrode 306 formed on the substrate 240 may depend on the radius R of the substrate 240. Thus, the negative electrode 306 may include a series of curved portions of increasing circumference (from the center of the substrate, for example). The first innermost curved portion of the negative electrode 306 may have smaller circumference than the second curved portion, and so on.

Similar to the negative electrode 306, the electrode 308 may include a plurality of circular tines of increasing diameter from a center of the substrate 240. The electrode 308 (interchangeably referred to as the positive electrode) includes a substantially straight portion 322 connecting the positive electrode 308 to the interconnecting wire 312. Herein, the straight portion 322 may be parallel to the straight portion 320 of the negative electrode 306 and may extend from an edge (from the circumference) of the substrate 240 inward towards the center of the substrate 240. As an example, a length of the straight portion 322 of the positive electrode 308 may be equal to or lesser than or greater than the length of the straight portion 320 of the negative electrode 306. The positive electrode 308 may additionally include a plurality of discrete curved portions 326 starting at certain locations along the straight portion 322 running counter-clockwise along the surface of the substrate 240 (away from the straight portion 320 of the negative electrode 306) and ending at a distance from the straight portion 322. Herein, each curved portion 326 of the positive electrode 308 corresponds to a major arc of a circle of certain radius with center coinciding with the center of the substrate 240 and the center of the curved portions 324 of the negative electrode 306, for example. As an example, an innermost curved portion 324 of the positive electrode 308 may be formed at the center of the substrate 240 and may further include a major arc of radius r1'. As such, the radius r1' may be greater than the radius r1 of the innermost curved portion of the negative electrode 306 and may be at a spacing x from the innermost curved portion of the negative electrode 306. A second curved portion of the positive electrode 308 may be formed at a spacing w' from the innermost curved portion of the positive electrode 308 and may include a major arc of radius r2' where r2'=r1'+w'. In effect, the radius r2=(r1+w+x). Likewise, a third curved portion of the positive electrode 308 is formed at a spacing w' from the second curved portion of the positive electrode 308, and further includes a major arc of radius r3', wherein r3'=r2'+w'=r1'+2w'. In a similar way, successive curved portions of the positive electrode 308 may be formed at the spacing w', and with increasing radii. Mathematically, the radius of the mth curved portion 326 of the positive electrode 308 may be given by equation (2):

$$r(m)' = r1' + (m-1)*w' \qquad (2)$$

The number, m of the curved portions 326 of the positive electrode 308 formed on the substrate 240 may depend on the radius R of the substrate 240, for example. In this way, the positive electrode 308 may be interdigitated with the negative electrode 306. In one example, the spacing, w between the negative electrodes may be equal to the spacing, w' between the positive electrodes. In another example, the spacing w may be different from the spacing w'. As mentioned earlier, various geometries of the interdigitated electrodes may be possible. FIG. 3B shows an example design of the circular interdigitated electrodes.

Turning to FIG. 3B, a schematic view 350 of the first surface of the sensor element 234 of FIG. 2A and the accompanying electric circuit 314 is shown. As mentioned earlier, the details of the substrate 240, the electric circuit 314 and the electrical interconnecting wires 310 and 312 are similar explained with reference to FIG. 3A. Briefly, the substrate 240 is manufactured from porous electrically insulating materials and may be circular in shape. The sensor element 234 includes a pair of circular interdigitated electrodes 352 and 356 formed on a surface of the sensor element 234. Herein, the pair of planar interdigitated electrodes 352 and 356 may form circular interdigitated tines indicated by black and grey lines in view 350. The details of the electrodes 352 and 354 may be similar to the electrodes 306 and 308 discussed earlier with reference to FIG. 3A. Briefly, the electrodes 352 and 354 may be composed of metals such as platinum, gold, and the like as described earlier, and may further be connected via electrical connections to the electric circuit 314. The electrode 354 of the sensor element 234 is a positive electrode connected to the positive terminal of the voltage source 316 of the electric circuit 314 via connecting wire 312. Likewise, the electrode 352 of the sensor element 234 is a negative electrode connected to the positive terminal of the voltage source 316 of the electric circuit 314 via connecting wire 310. As explained earlier, the electric circuit 314 and the interconnecting wires 310 and 312 are housed outside the exhaust passage 210 (as one example, <1 meter away). As explained earlier, the voltage source 316 and the measurement device 318 of the electric circuit 314 may be controlled by a controller, such as controller 12 of FIG. 1, so that particulate matter collected at the PM sensor assembly 202 may be used for diagnosing leaks in the DPF.

Similar to the negative electrode 306 shown in FIG. 3A, the negative electrode 352 includes a plurality of circular tines of increasing diameter from a center of the substrate 240. The negative electrode 352 includes a substantially straight portion 358 connecting the negative electrode 352 to the interconnecting wire 310. Herein, the straight portion 358 originates at a point along the circumference of the substrate 240 and extends horizontally inward towards the center of the substrate 240. The negative electrode 352 additionally includes a plurality of discrete curved portions 360 formed along the substrate. Herein, each curved portion 360 corresponds to a major arc of a circle of certain radius with center coinciding with the center of the substrate 240. In addition, the straight portion 358 may intersect each of the curved portions 360 of the negative electrode 352 at midpoints along the major arc, for example. Similar to the negative electrode 306 of FIG. 3A, from equation (1), the radius of the nth curved portion may be mathematically represented as r(n)=r1+(n-1)*w, where r1 is the radius of the innermost curved portion 360, and w is the spacing between successive curved portion 360 of the negative electrode 352.

Similar to the positive electrode 308 shown in FIG. 3A, the positive electrode 354 includes a plurality of circular tines of increasing diameter from a center of the substrate 240. In contrast to the positive electrode 308 shown in FIG. 3A, the positive electrode 354 includes a substantially straight portion 356 connecting the positive electrode 354 to the interconnecting wire 312. Herein, the straight portion 356 originates at a point along the circumference of the substrate 240 located diametrically opposite to the point of origin of the straight portion 358 of the negative electrode 352. In addition, the straight portion 356 may extend horizontally inward towards the center of the substrate 240. The negative electrode 352 may additionally include a plurality of discrete curved portions 362 formed along the substrate. Herein, each curved portion 362 corresponds to a major arc of a circle of certain radius with center coinciding with the center of the substrate 240, for example. In addition, the straight portion 356 may intersect each of the curved portion 362 at mid-points along the major arc, for example. Herein, the major arcs of the positive electrode 354 may be opposing to the major arcs of the negative electrode 352. Thus, the ends of the major arcs of the positive electrode 354 may be diametrically opposite to the ends of the major arcs of the negative electrode 352. Similar to the positive electrode 308 of FIG. 3A, the radius of the mth curved portion may be mathematically represented as $r(m)'=r1'+(m-1)*w'$ where $r1'$ is the radius of the innermost curved portion 362, and $w'$ is the spacing between successive curved portion 362. In this way, a pair of concentric interdigitated electrodes is formed on the circular substrate 240. In one example, the spacing w between the negative electrodes may be equal to the spacing $w'$ between the positive electrodes. In another example, the spacing w may be different from the spacing $w'$. In FIGS. 3A and 3B, the electrodes are composed of discrete major arcs arranged so as to form the interdigitated pattern. However, it is possible to form the interdigitated electrodes using continuous electrodes as shown in FIG. 3C.

Turning to FIG. 3C, a schematic view 375 of first surface of the sensor element 234 of FIG. 2A and the accompanying electric circuit 314 is shown. As mentioned earlier, the details of the substrate 240, the electric circuit 314 and the electrical interconnecting wires 310 and 312 are similar explained with reference to FIGS. 3A and 3B. Briefly, the sensor element 234 may be formed on a circular substrate 240 manufactured from porous electrically insulating material. The sensor element 234 includes a pair of spiraling interdigitated electrodes 376 and 378 formed on the first surface of the sensor element 234. Herein, the pair of spiraling interdigitated electrodes 376 and 378 are indicated by black and grey lines in view 375. The details of the electrodes 376 and 378 are similar to the electrodes 352 and 354 and electrodes 306 and 308 discussed earlier with reference to FIGS. 3A and 3B respectively. Briefly, the electrodes 376 and 378 may be composed of metals such as platinum, gold, and the like as described earlier, and may further be connected via electrical connections to the electric circuit 314. The electrode 376 of the sensor element 234 is a positive electrode connected to the positive terminal of the voltage source 316 of the electric circuit 314 via connecting wire 312. Likewise, the electrode 378 of the sensor element 234 is a negative electrode connected to the positive terminal of the voltage source 316 of the electric circuit 314 via connecting wire 310. As explained before, the electric circuit 314 and the interconnecting wires 310 and 312 are housed outside the exhaust passage 210 (as one example, <1 meter away). As explained earlier, the voltage source 316 and the measurement device 318 of the electric circuit 314 may be controlled by a controller, such as controller 12 of FIG. 1, so that particulate matter collected at the PM sensor assembly 202 may be used for diagnosing leaks in the DPF.

The positive electrode 376 includes a straight portion 380 and a curved portion 384 originating at an end of the straight portion 380 and spiraling along the circumference of the substrate inward with decreasing curvature towards the center of the substrate 240. Likewise, the negative electrode 378 includes a straight portion 382 at a distance w from the straight portion 380 of the positive electrode 376. In addition, the negative electrode 378 includes a curved portion 386 originating at an end of the straight portion 38 and spiraling along the circumference of the substrate inward with decreasing curvature towards the center of the substrate 240. Herein, the spacing between the curved portion 384 of the positive electrode 376 and the curved portion 386 of the negative electrode 378 is equal to the spacing w between the straight portions 380 and 382 of the positive and negative electrode.

As an example, while operating the PM sensor to accumulate soot particulates, the controller may send a control signal to the electric circuit 314 to apply a voltage to the electrodes 376 and 378 of the sensor element 234. The charged soot particulates may then be trapped between the spiraling positive electrode 376 and the spiraling negative electrode 378. Likewise, if the interdigitated electrodes of the sensor element have a layout similar to the layout shown in FIG. 3A or 3B, charged soot particulates may be trapped between the electrodes 306 and 308 or electrodes 352 and 354. As explained earlier, as the soot particles are deposited between the electrodes, the current measured between the electrodes may start to increase, which is measured by the measurement device 318. The controller 12 may be able to determine the current and infer a corresponding PM or soot load on the electrodes of the sensor element 234. By monitoring the load on the sensor element 234, the exhaust soot load downstream of the DPF may be determined, and thereby used to diagnose and monitor the health and functioning of the DPF. However, when the soot load of the sensor is higher than a threshold, the sensor element 234 may need to be regenerated. Herein, heating elements coupled to the second surface sensor element 234 may be operated to burn accumulated soot particle from the surface of sensor element 234 as shown in FIG. 4. For example, if the first surface including the interdigitated electrodes is a bottom surface, then the second surface of the sensor element including the heating elements is a top surface. The sensor element may be mounted such that the bottom surface is closer to the hole 244 of FIG. 2A. However, if the first surface including the interdigitated electrodes is a top surface, then the second surface including the heating elements is a bottom surface, and the sensor element may be flipped so that the top surface is closer to the hole 244 of FIG. 2A.

Turning now to FIG. 4, a schematic view 400 of a second surface of the sensor element 234 of FIG. 2A including a heating element 402 is shown. Herein, the second surface is opposite to the first surface including the interdigitated electrodes as explained with reference to FIGS. 3A-3C, for example. Thus, the electrodes and the heating elements are formed on opposite surfaces of the sensor element, therefore separated from each other by the thickness of the substrate of the sensor element, for example.

The heating element 402 may include, but is not limited to, a temperature sensor, and a heater. Possible materials for the heater and the temperature sensor forming the heating element may include platinum, gold, palladium, and the like; and alloys, oxides, and combinations comprising at least one of the foregoing materials, with platinum/alumina, platinum/palladium, platinum, and palladium. In view 400, the heating element 402 is a circular element having a radius smaller than the radius of the sensor element 234, for example. Various other geometries may be possible without deviating from the scope of the disclosure. Example geometries include rectangular, triangular, square, interdigitated electrodes, and the like. The heating element 402 may be used for regenerating the sensor element 234. Specifically, during conditions when the particulate matter load or soot load of the sensor element 234 is higher than a threshold, the heating element 402 may be operated to burn accumulated soot particles from the surface of sensor element.

During PM sensor regeneration, the controller 12 may send a control signal to a regeneration circuit 404 to apply a certain voltage to the heating element. For example, the regeneration circuit may be part of the electric circuit 314 of FIGS. 3A-3C and may include an additional voltage source 406, a switch 408 and connecting wires 410 and 412 connecting the voltage source 406 to the heating element 402. As an example, the controller may send a control signal to close the switch 408 in the regeneration circuit 404 for a threshold time to apply the voltage to the heating element 402 in order to raise the temperature of the heating element 402. Subsequently, when the sensor element 234 is sufficiently clean, the controller 12 may send a control signal to open the switch 408 in the regeneration circuit 404 to stop heating the heating element 402. By intermittently regenerating the sensor element 234, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter as explained in FIG. 8.

Thus, an example particulate matter sensor assembly includes a spherical assembly, a support rod coupled to a bottom end of the spherical assembly, a plurality of flow tubes coupled to a top end of the spherical assembly, and a sensor element positioned within the spherical assembly, distal to the plurality of flow tubes. Additionally or alternatively, wherein the spherical assembly comprises a hollow, inner device positioned concentrically within a hollow, outer device, the inner device separated from the outer device by a gap. Additionally or alternatively, wherein the plurality of flow tubes comprise an outer, cylindrical tube and an inner, cylindrical tube positioned coaxially within the outer tube, a length of the outer tube smaller than a length of the inner tube. Additionally or alternatively, the outer tube may be mounted to the top end of the spherical assembly via the hollow, outer device. Additionally or alternatively, the outer tube may include a plurality of perforations configured to receive exhaust from an exhaust passage, the exhaust received in the gap between the outer device and the inner device in a direction orthogonal to a plane of the sensor element, then exhaust may be directed through the gap towards a hole formed along a bottom portion of the inner device, the hole configured to direct the exhaust from the gap into the inner device towards the sensor element in a direction opposite to a direction of exhaust flow through the gap. Additionally or alternatively, the sensor element may include a pair of circular interdigitated electrodes formed on a first surface, and a heating element formed on a second opposite surface, wherein the sensor element may be suspendably coupled within the inner device via support legs attached to the inner device such that the pair of circular interdigitated electrodes face the hole on the inner device, and wherein the pair of circular interdigitated electrodes includes interdigitated spiraling positive and negative electrodes. Additionally or alternatively, the inner tube may be mounted to the top end of the spherical assembly via the hollow, inner device such that the inner device traverses the gap in the spherical assembly, wherein the exhaust received via the outer tube and directed into the inner device may be released into the exhaust passage via the inner tube. Additionally or alternatively, wherein the support rod may be hollow and may couple the spherical assembly to a bottom of an exhaust passage, and wherein the support rod may be configured to direct a portion of the exhaust received in the gap into the exhaust passage via a drainage hole of the support rod, the drainage hole positioned proximate to the bottom of the exhaust passage, wherein the portion of the exhaust includes exhaust particulates having a larger than threshold size.

Turning now to FIG. 2B, a schematic view 290 shows exhaust flow through the PM sensor assembly 202. Specifically, view 290 depicts exhaust flowing into the PM sensor assembly 202 via the plurality of perforations 250 formed along the curved surface of the outer tube 246. Herein, the plurality of perforations formed on the outer tube 246 is configured to receive exhaust from the exhaust passage and direct the exhaust into the gap 226 formed between the inner and the outer device. Directing the exhaust into the gap 226 includes directing the exhaust first into the space 228 between the outer tube 246 and the inner tube 248 as indicated by arrow 279 and then into the gap 226 as indicated by arrow 280. In particular, the exhaust enters the space 228 via the plurality of holes 250 in a direction parallel to the direction of exhaust flow (indicated by arrow 258) inside the exhaust passage 210.

As explained previously with reference to FIG. 2A, the top surface 272 is sealed. Therefore, the exhaust inside the space 228 is forced to travel downward (along Y-axis, as indicated by arrow 280) into the gap 226. Specifically, the exhaust flows in a direction perpendicular (as indicated by arrow 280) to each of the direction of exhaust flow inside the exhaust passage 210 (as indicated by arrow 258) and the direction of flow of exhaust into the space 228 (as indicated by arrow 279). The exhaust then spirals inside the gap 226, inside a region 232 enclosed within that gap 226, as indicated by arrow 280. In the schematic view 290, the gap 226 is an annulus formed between the inner and the outer device and thus, the region 232 includes an annular region in the gap 226. The exhaust inside the gap 226 flows towards the bottom portion of the spherical assembly 204.

Specifically, the exhaust inside the gap 226 is split into two flow paths; a larger portion flowing towards the hole 244 formed on the bottom portion of the inner device 218, and a smaller portion flowing towards the bottom portion 261 of the inner device 218. As such, larger or heavier contaminants and/or water droplets 281 (such as particulates having a larger than threshold size or weight) in the exhaust may gravitate towards the bottom of the outer device 216 and flow into the hollow support rod 208 (as indicated by arrow 283). Herein, the region 232 is fluidically coupled to the region 256 enclosed by the portion 254 of the hollow rod 208 that is inside the exhaust passage 210. Herein, the region 256 is a cylindrical region. In addition, the hollow rod 208 includes drainage hole 252 located closer to the bottom of the hollow rod 208, and the larger/heavier contaminants 281 may be directed out the spherical assembly 204 via the drainage hole 252 as indicated by arrow 285.

While larger and heavier contaminants 281 are directed towards the hollow rod 208, a larger fraction or portion of the exhaust inside the gap 226 is directed towards the hole 244 formed at the bottom of the inner device 218. Specifically, lighter soot particles in the exhaust are directed towards the sensor element 234 suspended within the inner device 218 as indicated by arrow 282. The positioning of the hole 244 with respect to the sensor element 234 has several advantages. Firstly, the hole 244 is positioned away from the plurality of perforations 250 of the flow tubes 206. Thus, issues of water droplets and larger contaminants at or near the perforations 250 may not impinge on the sensor element. Secondly, the sensor element 234 is positioned above the hole 244 such that the larger/heavier contaminants 281 present in the exhaust are directed away from the sensor element 234. As a result, the sensor surface is protected from larger contaminants, and fluctuations in the sensor output may be reduced.

As such, the exhaust flows from the region 232 enclosed within the gap 226 into a region 230 enclosed within the inner device 218 via the hole 244. The region 230 includes a spherical region encompassed within the inner device 218. Herein, the sensor element 234 is positioned within the region 230 (and not within the region 232, for example) and the exhaust is first directed towards the sensor element 234 as indicated by arrow 282. Specifically, lighter soot particulates in the exhaust are directed upwards (along Y-axis) normally towards the surface of the sensor element 234. Said another way, the exhaust is directed in a direction that is perpendicular to a plane of the sensor element 234 (which is along X-axis, for example). It may be appreciated that the exhaust is directed towards the first surface including the electrode and not towards the second surface of the sensor element 234 that includes the heating element 238. Soot particulates in the exhaust are accumulated between the interdigitated electrodes 236 of the sensor element 234 as described previously. Exhaust inside the region 230 is then directed upwards (along Y-axis, as indicated by arrow 284) towards the inner tube 248 that is coupled at the top of the inner device 218. It may be appreciated that the direction of flow of exhaust in the region 230 is opposite to the direction of flow of exhaust in the region 232. Further, the direction of flow of exhaust in the region 230 is perpendicular to the direction of flow of exhaust inside the exhaust passage 210 (arrow 258). Furthermore, the direction of flow of exhaust in the region 230 is perpendicular to the direction of flow of exhaust into the spherical assembly 204 (as indicated by arrow 279).

The exhaust in the region 230 enclosed within the inner device 218 flows upwards (parallel to central axis Y-Y', for example) into the inner tube 248 via the bottom surface 278 of the inner tube 248. Specifically, the exhaust flows from the region 230 into the cylindrical region 287 enclosed within the inner tube 248 via the bottom surface 278. The exhaust then flows via the top surface 274 of the inner tube 248 into the exhaust passage 210. Herein, the direction of flow of exhaust out the inner tube 248 is orthogonal to each of the direction of flow of exhaust inside the exhaust passage 210 (indicated by arrow 258), and direction of flow of exhaust into the spherical assembly 204 (as indicated by arrow 279). In this way, by using cylindrical flow tubes 206 configured with outer tube and inner tube, exhaust may be directed into and out of the spherical assembly 204 respectively. The symmetrical design of the inlet and the outlet tube eliminate manufacture process for specific sensor orientation at the installation and enhance the sensor repeatability.

To summarize, exhaust flows into a first region enclosed between the inlet and the outlet tubes via the perforations, and is then directed into a second region enclosed in the gap between the inner and the outer device. Likewise, the exhaust in the second region enclosed by the gap is directed towards a third, spherical region enclosed within the inner device and additionally towards a fourth, cylindrical region enclosed within the support rod. Herein, the exhaust inside the third region enclosed within the inner device is accumulated between the interdigitated electrodes of the sensor element and subsequently directed towards a fifth, cylindrical region enclosed within the inner tube and then out into the exhaust passage. It may be appreciated that while the exhaust flow path is described with reference to regions, it may additionally be explained with reference to volumes. Herein, each of the region described above encompasses a specific volume; the first region includes a first volume, and so on. Thus, exhaust flow may be interchangeably explained with reference to volumes.

Thus, an example particulate matter sensor comprises a pair of concentric interdigitated electrodes formed on a first surface of a circular sensor element, a heating element formed on a second surface of the circular sensor element, the second surface opposite the first surface, support legs suspending the circular sensor element within an inner hollow spherical protection device, and an outer, hollow spherical protection device for receiving exhaust flow from an exhaust pipe and directing the exhaust flow towards the circular sensor element, the inner protection device positioned concentrically within the outer protection device. Additionally or alternatively, the outer protection device may include a mounting rod and an outer cylindrical tube coupled to diametrically opposite portions of the outer protection device, the mounting rod further coupling the outer protection device to a bottom of the exhaust pipe. Additionally or alternatively, a larger portion of the exhaust may be directed inside the gap is diverted towards an orifice formed on the inner protection device while a smaller portion of the exhaust may be gravitated to the mounting rod, a size of exhaust particulates in the smaller portion being bigger than the size of exhaust particulates in the larger portion. Additionally or alternatively, the larger portion of the exhaust received at the orifice that is diverted into the inner protection device may be directed towards the pair of concentric interdigitated electrodes of the circular sensor element; and after passage through the sensor element, the larger portion of exhaust may be directed into an inner cylindrical tube coupled to a top portion of the inner protection device. Additionally or alternatively, the inner cylindrical tube may be positioned coaxially within the outer cylindrical tube and may be configured to direct the larger portion of the exhaust out of the particulate matter sensor and into the exhaust pipe. Additionally or alternatively, the mounting rod may include a drainage hole coupled to the bottom of the exhaust pipe to direct the particulates in the smaller portion of the exhaust out of the particulate matter sensor and into the exhaust pipe. Additionally or alternatively, the mounting rod may include a drainage hole located closer to the bottom of the exhaust pipe to direct particulates in the smaller portion of the exhaust out of the particulate matter sensor and into the exhaust pipe. Additionally or alternatively, the particulate matter sensor may further comprise a controller with computer readable instructions stored on non-transitory memory for applying positive and negative voltage to the pair of concentric interdigitated electrodes to accumulate particulates in the larger portion of the exhaust between the pair of concentric interdigitated electrodes, estimating a load on the sensor based on a current generated between the pair of concentric interdigitated electrodes of the circular sensor element. Responsive to the load being higher than a threshold, the controller may apply a voltage to the heating element to regenerate the sensor.

FIGS. 2A-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 5:
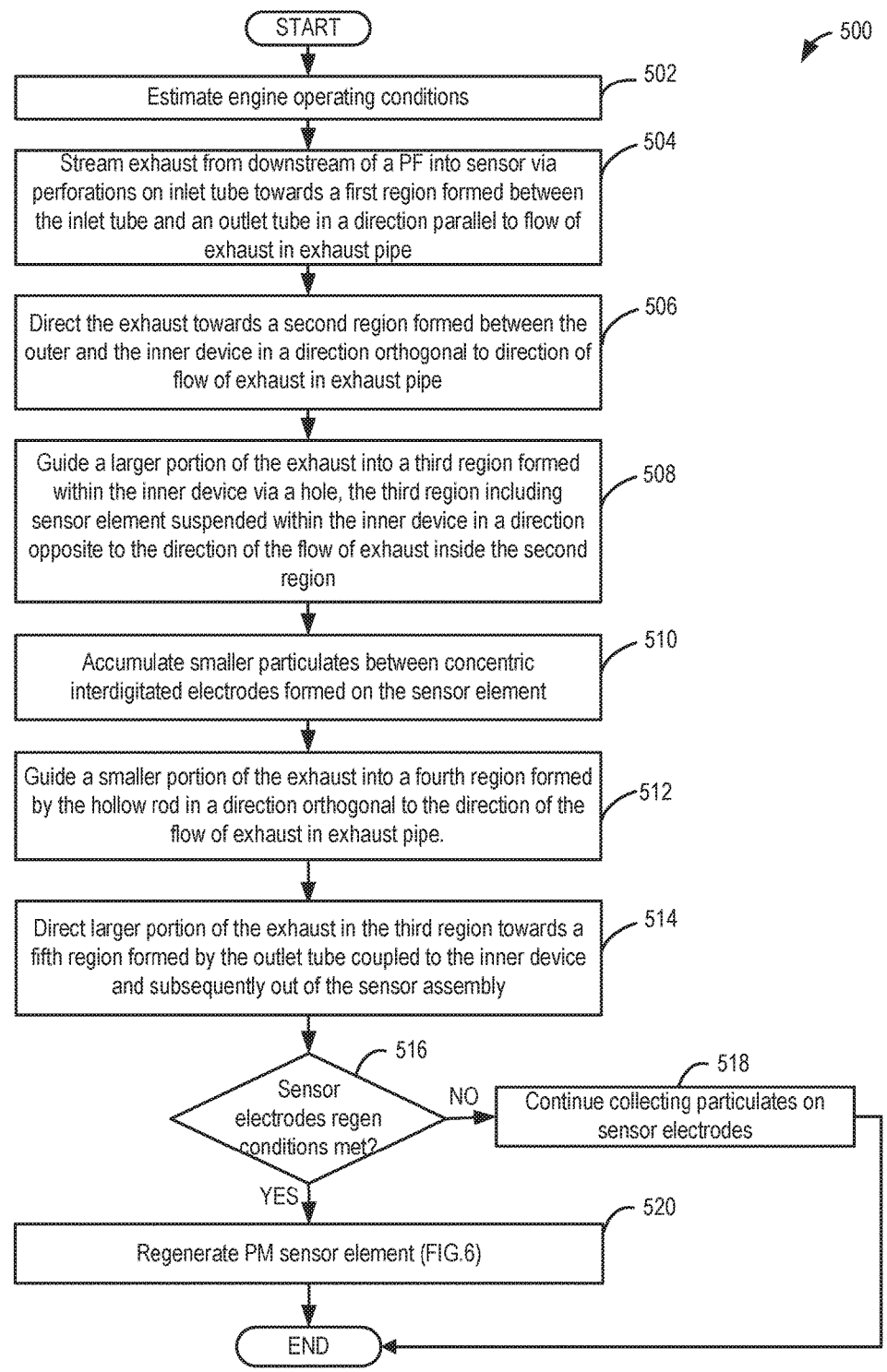
FIG. 5 shows a flow chart depicting an example method for accumulating particulates in the exhaust flow across the sensor element positioned within an inner device of the spherical assembly of the PM sensor.

Turning now to FIG. 5, a method 500 for accumulating particulates in the exhaust flow across sensor electrodes positioned within the PM sensor (such as a PM sensor 106 shown at FIG. 1, and/or PM sensor assembly 202 of FIGS. 2A and 2B, for example) is shown. Specifically, the particulates in the exhaust flow may be accumulated across interdigitated electrodes formed on a circular substrate and positioned within a spherical protection assembly of the PM sensor. Herein, the spherical assembly includes an inner spherical device positioned within an outer spherical device and separated by a gap. In addition, the spherical assembly includes flow tube attached to the top to direct exhaust in and out of the spherical assembly.

Instructions for carrying out method 500 and the rest of the methods 600 and 700 included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 502, method 500 includes determining and/or estimating engine-operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

Method 500 proceeds to 504 where a portion of exhaust flowing from downstream of a particulate filter (such as DPF 102 of FIG. 1) is directed into a PM sensor via perforations formed on an inlet tube. Herein, the inlet tube is an outer cylindrical tube with a plurality of perforations formed along the curved surface. Further, a cylindrical outlet tube may be positioned coaxially within the inlet tube and separated by a space. As explained earlier, the inlet tube has a larger diameter than the outlet tube, however, the length of the inlet tube is smaller than the length of the outlet tube. The portion of the exhaust flowing via the perforations of the inlet tube flows into a first region formed between the inlet and the outlet tube. Herein, the first region refers to the space between the inner and the outer tubes. The first region encloses a first volume there between, the first volume being the volume enclosed in the space between the inlet and the outlet tube. The direction of flow of exhaust into the inlet tube is parallel to the direction of flow of exhaust inside the exhaust pipe, for example.

Next, method 500 proceeds to 506. At 506, method 500 includes directing the portion of the exhaust from the first volume towards a second region in a direction orthogonal to the direction of flow of exhaust in the exhaust pipe. Herein, the second region refers to the gap formed between the inner and the outer device. For example, the first region is fluidically coupled to the second region, via a bottom surface of the inlet tube Method 500 proceeds to 508. At 508, method 500 includes guiding a larger portion of the exhaust in the second region into a third region via a hole that is formed at the bottom of the inner device. Herein, the third region is the region formed within the inner device that includes the sensor element. The sensor element is suspended within the inner device with the aid of support legs, for example. As such, the direction of flow of exhaust from the second region into the third region is in a direction opposite to the direction of the flow of exhaust inside the second region. In addition, the larger portion of the exhaust includes particulates having smaller than threshold size particulates (smaller particulates, for example). Method 500 proceeds to 510.

At 510, method 500 includes accumulating particulates in the larger portion of the exhaust across the electrodes of the sensor element. Specifically, at 510, smaller particulates in the larger portion of the exhaust are directed towards the electrodes of the sensor element and the smaller particulates are deposited across the electrodes. Herein, larger portion of the exhaust is directed normally towards the sensor element. As such, the direction of exhaust flow from the second region towards the third region is orthogonal to the direction exhaust flow inside the exhaust passage. As described previously, the sensor element including interdigitated electrodes is positioned closer to the hole. Thus, smaller soot particulates in the portion of the exhaust entering the third region via the hole are captured and accumulated across the concentric interdigitated electrodes of the sensor element. As explained previously, the sensor electrodes may include interdigitated major arcs or interdigitated spiraling electrodes. The positive electrodes are connected to the positive terminal of a voltage supply and the negative electrodes are connected to a measurement device and then to the negative terminal of the voltage supply. When the controller applies a voltage to the sensor electrodes, particulates inside the third region may experience a strong electric field, enabling them to be accumulated between the electrodes. In addition, a load on the sensor electrodes is estimated based on a current generated in the sensor electrodes. When particulates accumulate on the surface of the sensor electrodes, the resistance of the electrodes starts decreasing and a current measured by the measurement device starts to increase. The controller may be able to deduce a load on the sensor electrodes based on the current measured across the electrodes. Method 500 then proceeds to 512.

Method 500 proceeds to 512. At 512, method 500 includes directing a smaller portion of the exhaust inside the second region towards a fourth region, the fourth region formed within a hollow rod. While smaller particulates in the exhaust are directed upwards towards the hole and then towards the sensor element (e.g., at 508 and 510 of method 500), larger particulates (such as particulates having larger than the threshold size) in the exhaust may gravitate towards the bottom of the outer device at 512. Thus, the smaller portion of the exhaust and the larger portion of the exhaust flow in opposite directions, further flowing orthogonal to the direction of flow of exhaust in the exhaust pipe. As described previously, the hollow rod is fluidically coupled to the bottom of the outer device. Thus, the larger particulates collecting at the bottom of the outer device travel into the fourth region enclosed by the hollow rod. In addition, the hollow rod a drainage hole located closer to the bottom of the hollow rod. Thus, the larger particulates in the smaller portion of the exhaust inside the fourth region are directed towards the drainage hole on the hollow rod, and thereby drained out of the assembly. In this way, by separating the particulates and directing the larger particulates away from the sensor element, and further directing the larger particulates and water droplets towards the drainage holes in the hollow rod, larger particulates may not be able to deposit on the sensor element. Therefore, sensor errors due to these particulates depositing on the sensitive electrode surface, may be reduced. Method proceeds to 514.

At 514, method 500 includes guiding the larger portion of the exhaust inside the third region formed within the inner device towards a fifth region formed within the outlet tube in a direction orthogonal to the direction of the flow of exhaust in exhaust pipe. Guiding the larger portion of the exhaust into the fifth region includes guiding the larger portion of the exhaust from the third region of the inner device into the fifth region formed within the outlet tube via the bottom of the outlet tube that is coupled to the top portion of the inner device. Herein, the outlet tube is fluidically coupled to the top of the inner device, at an end that is diametrically opposite to the hole of the inner device, for example. In addition, the larger portion of the exhaust is directed out of the fifth region and into the exhaust pipe via a top of the outlet tube in a direction orthogonal to the direction of flow of exhaust inside the exhaust pipe. Method 500 then proceeds to 516.

At 516, method 500 includes intermittently checking if the sensor electrode has met the regeneration conditions. Specifically, when the soot load on the PM sensor is greater than the threshold, or when a resistance of the PM sensor (adjusted for temperature) drops to a threshold resistance, or when a current of the PM sensor is greater than a threshold current, PM sensor regeneration conditions may be considered met. In some examples, if a threshold time has elapsed since an immediately previous sensor regeneration, regeneration condition may be considered met. The PM sensor may require regeneration to enable further PM detection.

Figure 6:
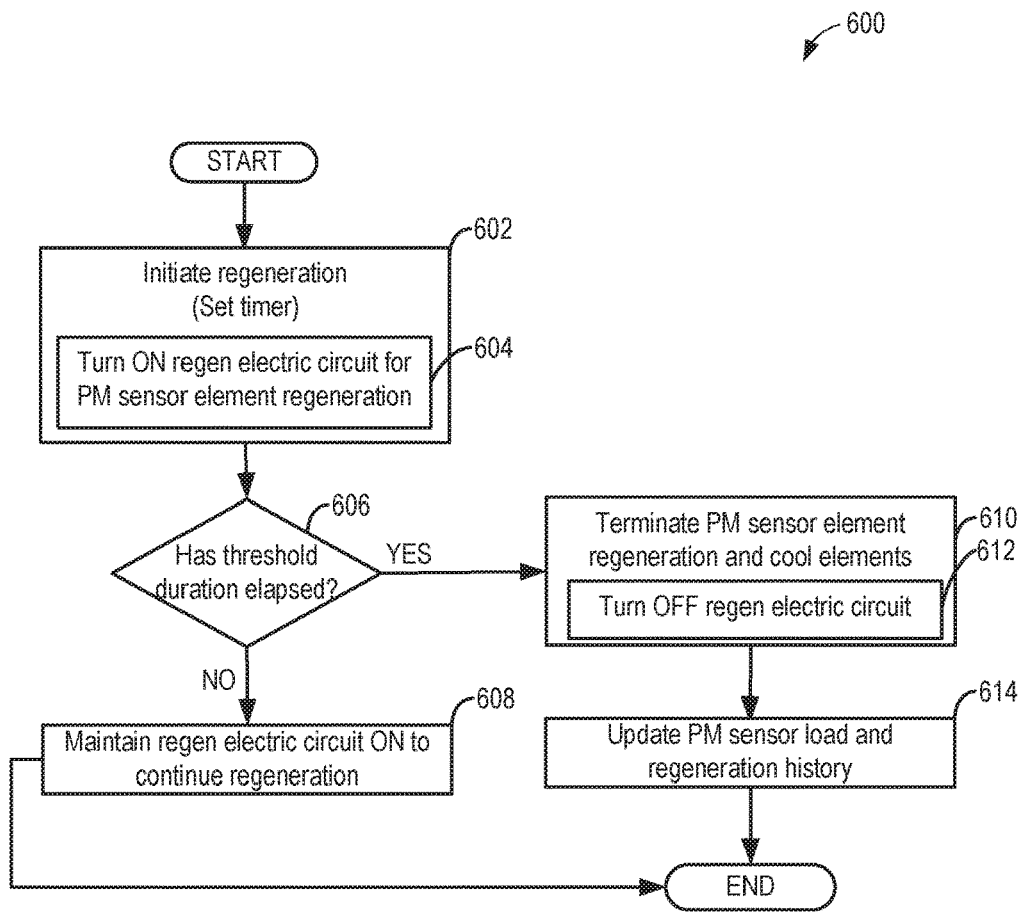
FIG. 6 is a flow chart depicting an example method for regenerating the sensor electrodes of the PM sensor.

If regeneration conditions are met (e.g., "YES" at 516), then method 500 proceeds to 520 where the PM sensor may be regenerated by performing a method described in FIG. 6. Briefly, regeneration of the PM sensor may be initiated by heating up the sensor. The PM sensor may be heated by actuating a heating element formed on a different surface of the sensor element that is opposite to the surface including the electrodes, for example. Herein, the controller may close the switch in a regeneration circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes. However, if PM sensor regeneration conditions are not met (e.g., "NO" at 516), then method proceeds to 518 where the particulates may continue to be collected on the sensor electrodes and the method ends.

Thus, an example method may include streaming exhaust from downstream of a particulate filter into the exhaust sensor assembly via perforations formed on an inlet tube towards a first region formed between the inlet tube and an outlet tube in a direction parallel to flow of exhaust in an exhaust pipe. Herein the inlet tube may be coupled to a top of an outer, hollow device, and the method may include directing the exhaust from the first region towards a second region formed between the outer device and an inner, hollow device in a direction orthogonal to the flow of exhaust in the exhaust pipe. The inner device may be positioned concentrically within the outer device. Additionally or alternatively, the method may further comprise guiding a larger portion of the exhaust inside the second region towards a third region formed within the inner device via a hole located at a bottom of the inner device in a direction opposite to the direction of the flow of exhaust inside the second region. The third region may include a sensor element suspended within the inner device. Additionally or alternatively, the method may include directing a smaller portion of the exhaust in the second region into a fourth region, the fourth region being enclosed within a hollow rod of the sensor assembly, wherein the hollow rod may be coupled to a bottom portion of the outer device. Additionally or alternatively, the method may further comprise applying a voltage to concentric interdigitated electrodes of the sensor element to accumulate particulates in the larger portion of the exhaust between the electrodes and directing the larger portion of the exhaust first into a fifth region formed by an outlet tube coupled to a top end of the inner device and subsequently out of the sensor assembly. Additionally or alternatively, the method may further comprise flowing particulates in the smaller portion of the exhaust inside the fourth region towards a drainage hole located at a bottom end of the hollow rod and draining the particulates at the drainage hole, the hollow rod coupling the exhaust sensor assembly to a bottom of the exhaust pipe.

Turning now to FIG. 6, a method 600 for regenerating the PM sensor (such as a PM sensor 106 shown at FIG. 1, and/or PM sensor assembly 201 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 602, regeneration of the PM sensor may be initiated and the PM sensor may be regenerated by heating up the sensor at 604. The PM sensor may be heated by actuating a heating element until the soot load of the sensor has been sufficiently reduced by oxidation of the carbon particles between the electrodes. The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration and the method ends. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine-operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
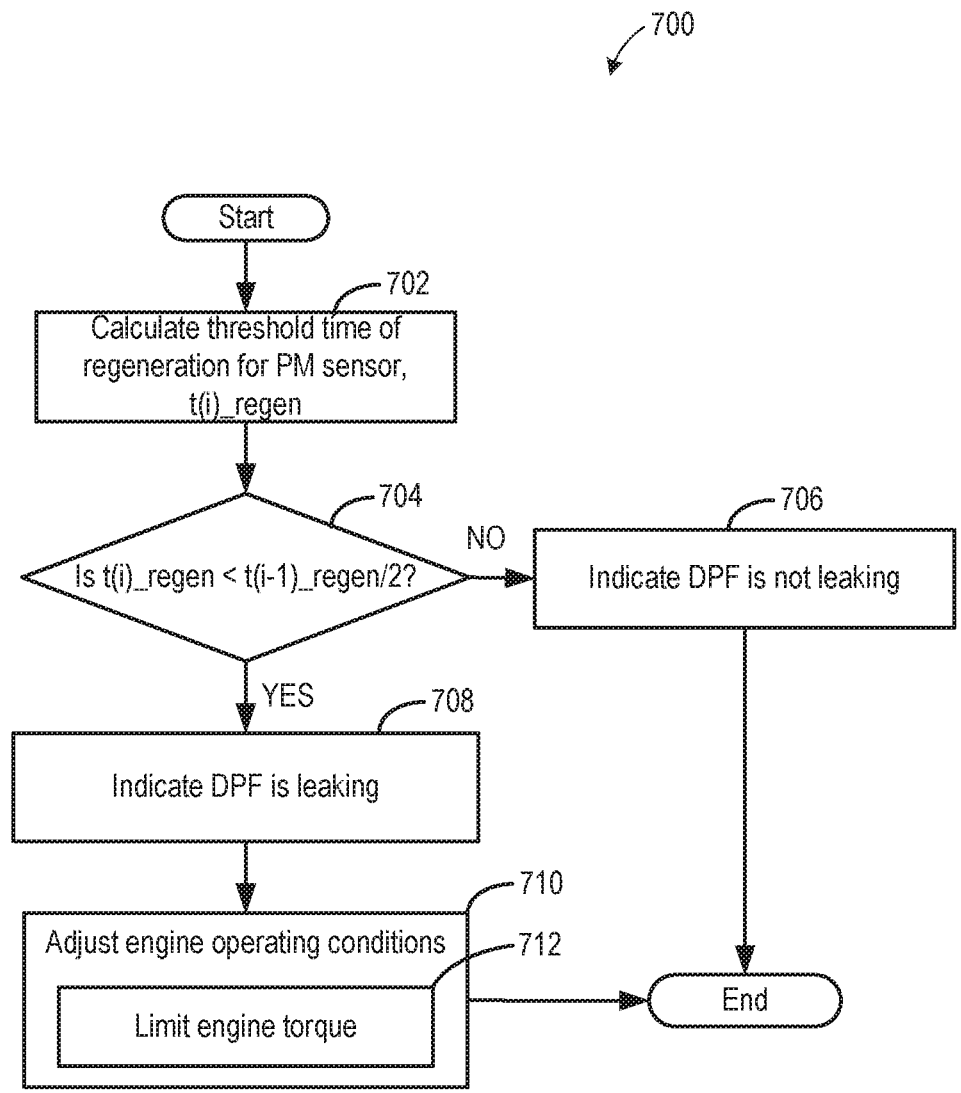
FIG. 7 shows a flow chart depicting an example method for diagnosing leaks in a particulate filter positioned upstream of the PM sensor.
Figure 8:
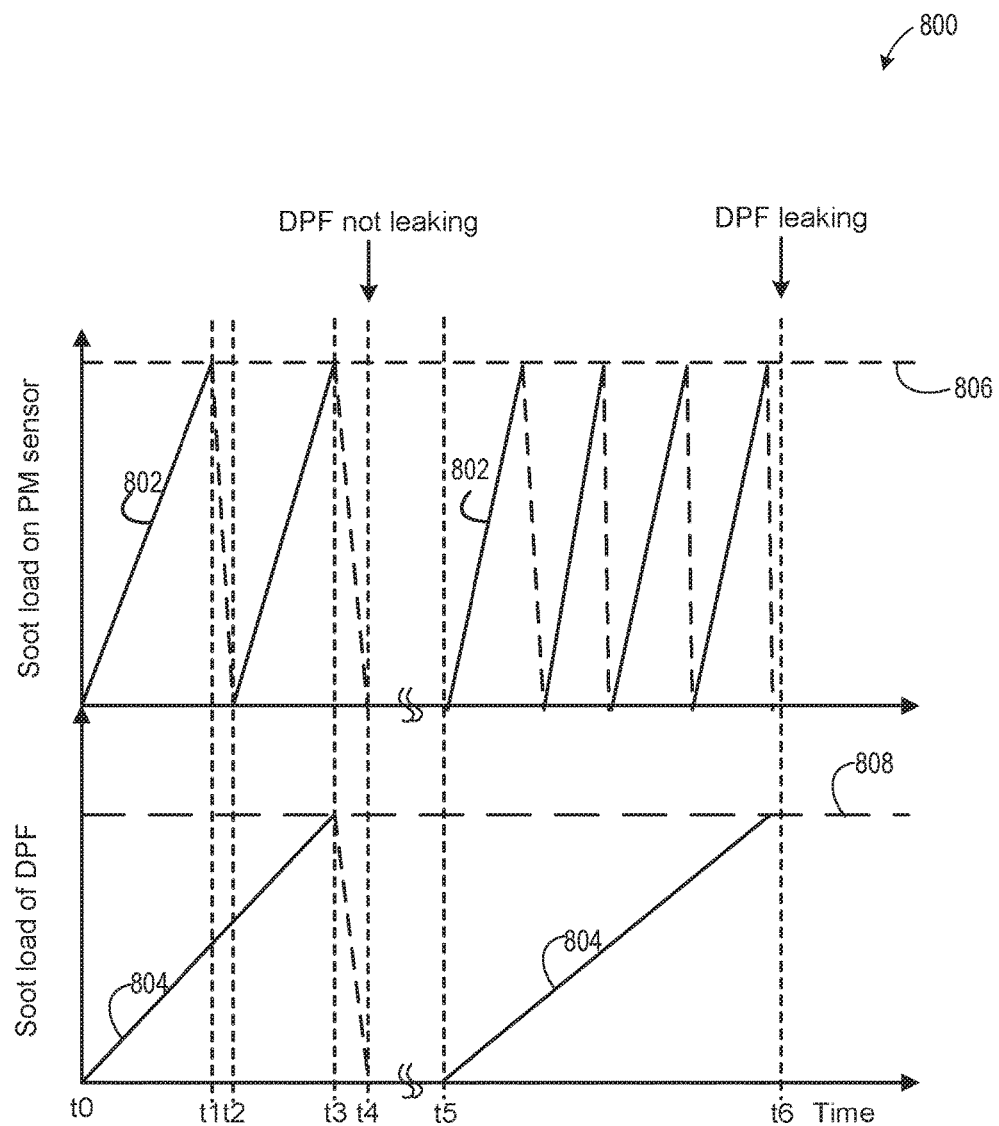
FIG. 8 shows an example relationship between a soot load on the PM sensor, and a soot load on a particulate filter positioned upstream of the PM sensor.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i-1)_regen, which is the previously calibrated time of regeneration of the PM sensor. From this, it may be inferred that the soot sensor may cycle through regeneration multiple times in order to diagnose the DPF. If the t(i)_regen is less than half the value of t(i-1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and DPF.

The first plot of FIG. 8 shows a soot load on the PM sensor. As previously described, PM gets deposited across the circular positive and negative electrodes formed on a circular substrate that is positioned inside an inner device closer to a hole formed at the bottom of the inner device, for example. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, as PM continues to accumulate, the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may require regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804)

reaches the threshold soot load for DPF regeneration (marker 808). Between t3 and t4, the DPF may be regenerated to burn off the soot deposited on the DPF. Further at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended.

In this way, a sensor element may be shielded by two spherical protective tubes that further enhance uniform soot deposition. Exhaust gases may enter the sensor assembly via perforations formed on the outer inlet tube. As such, the exhaust may undergo changes in flow direction which helps reduce flow rate. In addition, the exhaust may be directed towards the sensor element positioned within the inner device via a hole formed on the bottom of the inner device. Herein, the hole may be distanced from the inlet tube so as to separate the inlet tube from the sensor element. In this way, by separating the inlet tube from the sensor element, issues of water droplets and larger contaminants impinging on the sensor element and causing fluctuations in the sensor output may be reduced. Further, the hole on the inner device may be sized, shaped, and positioned to generate uniform flow of exhaust gases onto the sensor surface.

A technical effect of greater uniform flow impingement of sample gasses on a particulate matter sensor may be achieved by decreasing the flow speed of the exhaust gas. By interrupting the flow path of the exhaust gas, and decreasing its speed, the uniformity of the flow on the particulate matter sensor surface may be increased. Further still, by positioning the sensor element away from the inlet tube and additionally mounting the assembly on a hollow rod, the particulate matter sensor may be shielded from contamination by larger particulates and water droplets. Further, drainage holes formed at the bottom of the hollow may drain the contaminants out of the sensor assembly.

The systems and methods described above provide for a particulate matter sensor assembly comprising a spherical assembly, a support rod coupled to a bottom end of the spherical assembly, a plurality of flow tubes coupled to a top end of the spherical assembly, and a sensor element positioned within the spherical assembly, distal to the plurality of flow tubes. In a first example of the particulate matter sensor assembly, the sensor may additionally or alternatively include wherein the spherical assembly comprises a hollow, inner device positioned concentrically within a hollow, outer device, the inner device separated from the outer device by a gap. A second example of the particulate matter sensor assembly optionally includes the first example and further includes wherein the plurality of flow tubes comprise an outer cylindrical tube and an inner cylindrical tube positioned coaxially within the outer tube, a length of the outer tube smaller than a length of the inner tube. A third example of the particulate matter sensor assembly optionally includes one or more of the first and the second examples, and further includes wherein the outer tube is mounted to a top end of the spherical assembly via the hollow, outer device. A fourth example of the particulate matter sensor assembly optionally includes one or more of the first through the third examples, and further includes wherein the outer tube includes a plurality of perforations configured to receive exhaust from an exhaust passage, the exhaust received in the gap between the outer device and the inner device in a direction orthogonal to a plane of the sensor element, then the exhaust directed through the gap towards a hole formed along a bottom portion of the inner device, the hole configured to direct the exhaust from the gap into the inner device towards the sensor element in a direction opposite to a direction of exhaust flow through the gap. A fifth example of the particulate matter sensor assembly optionally includes one or more of the first through the fourth examples, and further includes wherein the sensor element includes a pair of circular interdigitated electrodes formed on a first surface, and a heating element formed on a second opposite surface, wherein the sensor element is suspendably coupled within the inner device via support legs attached to the inner device such that the pair of circular interdigitated electrodes face the hole on the inner device and wherein the pair of circular interdigitated electrodes includes interdigitated spiraling positive and negative electrodes. A sixth example of the particulate matter sensor assembly optionally includes one or more of the first through the fifth examples, and further includes wherein the inner tube is mounted to the top end of the spherical assembly via the hollow, inner device such that the inner device traverses the gap in the spherical assembly, wherein the exhaust received via the outer tube and directed into the inner device is released into the exhaust passage via the inner tube. A seventh example of the particulate matter sensor assembly optionally includes one or more of the first through the fifth examples, and further includes wherein the support rod is hollow and couples the spherical assembly to a bottom of an exhaust passage, and wherein the support rod is configured to direct a portion of the exhaust received in the gap into the exhaust passage via a drainage hole of the support rod, the drainage hole positioned proximate to the bottom of the exhaust passage, wherein the portion of the exhaust includes exhaust particulates having a larger than threshold size.

The systems and methods described above provide for a system comprising a particulate matter (PM) sensor located downstream of a particulate filter in an exhaust passage, the PM sensor comprising a pair of concentric interdigitated electrodes formed on a first surface of a circular sensor element, a heating element formed on a second surface of the circular sensor element, the second surface opposite the first surface, support legs suspending the circular sensor element within an inner hollow spherical protection device, and an outer hollow spherical protection device for receiving exhaust flow from an exhaust pipe and directing the exhaust flow towards the circular sensor element, the inner protection device positioned concentrically within the outer protection device. In a first example of the particulate matter sensor, the sensor may additionally or alternatively include wherein the outer protection device includes a mounting rod and an outer cylindrical tube coupled to diametrically opposite portions of the outer protection device, the mounting rod further coupling the outer protection device to a bottom of the exhaust pipe. A second example of the particulate matter sensor optionally includes the first example and further includes wherein the outer cylindrical tube comprises a plurality of holes configured to direct exhaust from the exhaust pipe first into a gap between the inner protection device and the outer protection device. A third example of the particulate matter sensor optionally includes one or more of the first and the second examples, and further includes wherein a larger portion of the exhaust directed inside the gap is diverted towards an orifice formed on the inner protection device while a smaller portion of the exhaust is gravitated to the mounting rod, a size of exhaust particulates in the smaller portion being bigger than the size of exhaust particulates in the larger portion. A fourth example of the particulate matter sensor optionally includes one or more of the first through the third examples, and further includes wherein the larger portion of the exhaust received at the orifice that is diverted into the inner protection device is directed towards the pair of concentric interdigitated electrodes of the circular sensor element; and after passage through the sensor element, the larger portion of exhaust is directed into an inner cylindrical tube coupled to a top portion of the inner protection device. A fifth example of the particulate matter sensor optionally includes one or more of the first through the fourth examples, and further includes wherein the inner cylindrical tube is positioned coaxially within the outer cylindrical tube and is configured to direct the larger portion of the exhaust out of the particulate matter sensor and into the exhaust pipe. A sixth example of the particulate matter sensor optionally includes one or more of the first through the fifth examples, and further includes wherein the mounting rod includes a drainage hole coupled to the bottom of the exhaust pipe to direct the particulates in the smaller portion of the exhaust out of the particulate matter sensor and into the exhaust pipe. A seventh example of the particulate matter sensor optionally includes one or more of the first through the sixth examples, and further comprising a controller with computer readable instructions stored on non-transitory memory for applying positive and negative voltage to the pair of concentric interdigitated electrodes to accumulate particulates in the larger portion of the exhaust between the pair of concentric interdigitated electrodes, estimating a load on the sensor based on a current generated between the pair of concentric interdigitated electrodes of the circular sensor element, and responsive to the load being higher than a threshold, applying a voltage to the heating element to regenerate the sensor.

The systems and methods described above also provide for a method, the method comprising streaming exhaust from downstream of a particulate filter into the exhaust sensor assembly via perforations formed on an inlet tube towards a first region formed between the inlet tube and an outlet tube in a direction parallel to flow of exhaust in an exhaust pipe, the inlet tube coupled to a top of an outer, hollow device, and directing the exhaust towards a second region formed between the outer device and an inner, hollow device in a direction orthogonal to the flow of exhaust in the exhaust pipe, the inner device positioned concentrically within the outer device. In a first example of the method, the method may additionally or alternatively include guiding a larger portion of the exhaust inside the second region towards a third region formed within the inner device via a hole located at a bottom of the inner device in a direction opposite to the direction of the flow of exhaust inside the second region, the third region including a sensor element suspended within the inner device, and directing a smaller portion of the exhaust in the second region into a fourth region, the fourth region being enclosed within a hollow rod of the sensor assembly, the hollow rod being coupled to a bottom portion of the outer device. A second example of the method optionally includes the first example, and further includes applying a voltage to concentric interdigitated electrodes of the sensor element to accumulate particulates in the larger portion of the exhaust between the electrodes and directing the larger portion of the exhaust first into a fifth region formed by an outlet tube coupled to a top end of the inner device and subsequently out of the sensor assembly. A third example of the method optionally includes one or more of the first and the second examples, and further includes flowing particulates in the smaller portion of the exhaust inside the fourth region towards a drainage hole located at a bottom end of the hollow rod and draining the particulates at the drainage hole, the hollow rod coupling the exhaust sensor assembly to a bottom of the exhaust pipe.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, 1-4, 1-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter sensor assembly, comprising:
a spherical assembly;
a support rod coupled to a bottom end of the spherical assembly;
a plurality of flow tubes coupled to a top end of the spherical assembly; and
a sensor element positioned within the spherical assembly, distal to the plurality of flow tubes.

2. The assembly of claim 1, wherein the spherical assembly comprises a hollow, inner device positioned concentrically within a hollow, outer device, the inner device separated from the outer device by a gap.

3. The assembly of claim 2, wherein the plurality of flow tubes comprises an outer, cylindrical tube and an inner, cylindrical tube positioned coaxially within the outer tube, a length of the outer tube smaller than a length of the inner tube.

4. The assembly of claim 3, wherein the outer tube is mounted to the top end of the spherical assembly via the hollow, outer device.

5. The assembly of claim 3, wherein the outer tube includes a plurality of perforations configured to receive exhaust from an exhaust passage, the exhaust received in the gap between the outer device and the inner device in a direction orthogonal to a plane of the sensor element, then exhaust is directed through the gap towards a hole formed along a bottom portion of the inner device, the hole configured to direct the exhaust from the gap into the inner device towards the sensor element in a direction opposite to a direction of exhaust flow through the gap.

6. The assembly of claim 5, wherein the sensor element includes a pair of circular interdigitated electrodes formed on a first surface, and a heating element formed on a second opposite surface, wherein the sensor element is suspendably coupled within the inner device via support legs attached to the inner device such that the pair of circular interdigitated electrodes faces the hole on the inner device, and wherein the pair of circular interdigitated electrodes includes interdigitated spiraling positive and negative electrodes.

7. The assembly of claim 5, wherein the inner tube is mounted to the top end of the spherical assembly via the hollow, inner device such that the inner tube traverses the gap in the spherical assembly, wherein the exhaust received via the outer tube and directed into the inner device is released into the exhaust passage via the inner tube.

8. The assembly of claim 5, wherein the support rod is hollow and couples the spherical assembly to a bottom of the exhaust passage, and wherein the support rod is configured to direct a portion of the exhaust received in the gap into the exhaust passage via a drainage hole of the support rod, the drainage hole positioned proximate to the bottom of the exhaust passage, wherein the portion of the exhaust includes exhaust particulates having a larger than threshold size.

9. A particulate matter sensor, comprising:
a pair of concentric interdigitated electrodes formed on a first surface of a circular sensor element;
a heating element formed on a second surface of the circular sensor element, the second surface opposite the first surface;
support legs suspending the circular sensor element within an inner, hollow spherical protection device; and
an outer, hollow spherical protection device for receiving exhaust flow from an exhaust pipe and directing the exhaust flow towards the circular sensor element, the inner protection device positioned concentrically within the outer protection device.

10. The particulate matter sensor of claim 9, wherein the outer protection device includes a mounting rod and an outer cylindrical tube coupled to diametrically opposite portions of the outer protection device, the mounting rod further coupling the outer protection device to a bottom of the exhaust pipe.

11. The particulate matter sensor of claim 10, wherein the outer cylindrical tube comprises a plurality of holes configured to direct exhaust from the exhaust pipe into a gap between the inner protection device and the outer protection device.

12. The particulate matter sensor of claim 11, wherein a larger portion of the exhaust directed inside the gap is diverted towards an orifice formed on the inner protection device while a smaller portion of the exhaust is gravitated to the mounting rod, a size of exhaust particulates in the smaller portion being bigger than a size of exhaust particulates in the larger portion.

13. The particulate matter sensor of claim 12, wherein the larger portion of the exhaust received at the orifice that is diverted into the inner protection device is directed towards the pair of concentric interdigitated electrodes of the circular sensor element; and after passage through the sensor element, the larger portion of exhaust is directed into an inner cylindrical tube coupled to a top portion of the inner protection device.

14. The particulate matter sensor of claim 13, wherein the inner cylindrical tube is positioned coaxially within the outer cylindrical tube and is configured to direct the larger portion of exhaust out of the particulate matter sensor and into the exhaust pipe.

15. The particulate matter sensor of claim 12, wherein the mounting rod includes a drainage hole coupled to the bottom of the exhaust pipe to direct the particulates in the smaller portion of the exhaust out of the particulate matter sensor and into the exhaust pipe.

16. The particulate matter sensor of claim 12, further comprising a controller with computer readable instructions stored on non-transitory memory for:
applying positive and negative voltage to the pair of concentric interdigitated electrodes to accumulate particulates in the larger portion of the exhaust between the pair of concentric interdigitated electrodes;
estimating a load on the particulate matter sensor based on a current generated between the pair of concentric interdigitated electrodes of the circular sensor element; and
responsive to the load being higher than a threshold, applying a voltage to the heating element to regenerate the particulate matter sensor.

* * * * *